United States Patent
O'Connor et al.

(10) Patent No.: US 7,713,711 B2
(45) Date of Patent: May 11, 2010

(54) ELECTRONIC METHODS FOR THE DETECTION OF ANALYTES

(75) Inventors: Stephen D. O'Connor, Pasadena, CA (US); Jon Faiz Kayyem, Pasadena, CA (US); Thomas J. Meade, Altadena, CA (US)

(73) Assignee: Osmetech Technology Inc., Pasadena, CA (US)

( * ) Notice: Subject to any disclaimer, the term of this patent is extended or adjusted under 35 U.S.C. 154(b) by 0 days.

(21) Appl. No.: 11/981,735

(22) Filed: Oct. 30, 2007

(65) Prior Publication Data

US 2008/0237061 A1 Oct. 2, 2008

Related U.S. Application Data

(63) Continuation of application No. 09/096,593, filed on Jun. 12, 1998, now Pat. No. 7,560,237.

(60) Provisional application No. 60/049,489, filed on Jun. 12, 1997.

(51) Int. Cl.
*G01N 33/00* (2006.01)
*G01N 33/53* (2006.01)

(52) U.S. Cl. .................. 435/7.1; 435/7.21; 436/501; 436/518

(58) Field of Classification Search .................. None
See application file for complete search history.

(56) References Cited

U.S. PATENT DOCUMENTS

| | | | |
|---|---|---|---|
| 3,963,522 A | 6/1976 | Harada et al. | |
| 4,072,576 A | 2/1978 | Arwin et al. | |
| 4,713,347 A | 12/1987 | Mitchell et al. | |
| 4,735,907 A | 4/1988 | Schaeffer et al. | |
| 4,819,658 A | 4/1989 | Kolodner | |
| 4,920,047 A | 4/1990 | Giaever et al. | |
| 4,964,972 A | 10/1990 | Sagiv et al. | |
| 5,089,112 A | 2/1992 | Skotheim et al. | |
| 5,108,573 A | 4/1992 | Rubinstein et al. | |
| 5,156,810 A | 10/1992 | Ribi | |
| 5,164,319 A | 11/1992 | Hafeman et al. | |
| 5,171,853 A | 12/1992 | Thorp et al. | |
| 5,180,968 A | 1/1993 | Bruckenstein et al. | |
| 5,187,096 A | 2/1993 | Giaever et al. | |
| 5,192,507 A | 3/1993 | Taylor et al. | |
| 5,194,133 A | 3/1993 | Clark et al. | |
| 5,200,051 A | 4/1993 | Cozzette et al. | |
| 5,242,828 A | 9/1993 | Bergstrom et al. | |
| 5,262,035 A | 11/1993 | Gregg et al. | |
| 5,320,725 A | 6/1994 | Gregg et al. | |
| 5,324,457 A | 6/1994 | Zhang et al. | |
| 5,356,786 A | 10/1994 | Heller et al. | |
| 5,391,272 A | 2/1995 | O'Daly et al. | |
| 5,403,451 A | 4/1995 | Riviello et al. | |
| 5,443,701 A | 8/1995 | Willner et al. | |
| 5,491,097 A | 2/1996 | Ribi et al. | |
| 5,534,132 A | 7/1996 | Vreeke et al. | |
| 5,571,568 A | 11/1996 | Ribi et al. | |
| 5,585,646 A * | 12/1996 | Kossovsky et al. | ............ 257/40 |
| 5,591,578 A | 1/1997 | Meade et al. | |
| 5,605,662 A | 2/1997 | Heller et al. | |
| 5,620,850 A | 4/1997 | Bamdad et al. | |
| 5,632,957 A | 5/1997 | Heller et al. | |
| 5,705,348 A | 1/1998 | Meade et al. | |
| 5,763,191 A | 6/1998 | Knoll et al. | |
| 5,770,369 A | 6/1998 | Meade et al. | |
| 5,780,324 A | 7/1998 | Tokura et al. | |
| 5,783,056 A | 7/1998 | Hampp et al. | |
| 5,824,483 A | 10/1998 | Meade et al. | |
| 5,874,316 A | 2/1999 | Cornell et al. | |
| 5,922,183 A | 7/1999 | Rauh | |
| 5,942,388 A | 8/1999 | Willner et al. | |
| 5,952,172 A | 9/1999 | Meade et al. | |
| 5,972,199 A | 10/1999 | Heller et al. | |
| 6,013,170 A | 1/2000 | Meade | |
| 6,013,459 A * | 1/2000 | Meade | ............ 435/7.1 |
| 6,060,327 A * | 5/2000 | Keen | ............ 506/9 |
| 6,063,573 A | 5/2000 | Kayyem | |
| 6,071,699 A | 6/2000 | Meade et al. | |
| 6,087,100 A | 7/2000 | Meade et al. | |
| 6,090,545 A * | 7/2000 | Wohlstadter et al. | ............ 435/6 |
| 6,090,933 A | 7/2000 | Kayyem et al. | |
| 6,096,273 A * | 8/2000 | Kayyem et al. | ............ 422/68.1 |
| 6,177,250 B1 | 1/2001 | Meade et al. | |
| 6,180,352 B1 | 1/2001 | Meade et al. | |

(Continued)

FOREIGN PATENT DOCUMENTS

EP 0 339 821 A1 11/1989

(Continued)

OTHER PUBLICATIONS

Agladze (Metallurgy and Foundry Engineering, 1997, 23(2), 127-137).

(Continued)

*Primary Examiner*—Lisa V Cook
(74) *Attorney, Agent, or Firm*—Morgan, Lewis & Bockius LLP; Robin M. Silva; Tao Huang

(57) ABSTRACT

The present invention is directed to the detection of target analytes using electronic techniques, particularly AC techniques.

9 Claims, 8 Drawing Sheets

U.S. PATENT DOCUMENTS

| | | |
|---|---|---|
| 6,200,761 B1 | 3/2001 | Meade et al. |
| 6,221,583 B1 | 4/2001 | Kayyem et al. |
| 6,232,062 B1 | 5/2001 | Kayyem et al. |
| 6,238,870 B1 | 5/2001 | Meade et al. |
| 6,248,229 B1 | 6/2001 | Meade |
| 6,258,545 B1 | 7/2001 | Meade et al. |
| 6,264,825 B1 | 7/2001 | Blackburn et al. |
| 6,268,149 B1 | 7/2001 | Meade et al. |
| 6,268,150 B1 | 7/2001 | Meade et al. |
| 6,277,576 B1 | 8/2001 | Meade et al. |
| 6,290,839 B1 | 9/2001 | Kayyem et al. |
| 6,479,240 B1 | 11/2002 | Kayyem et al. |
| 6,495,323 B1 | 12/2002 | Kayyem et al. |
| 6,528,266 B2 | 3/2003 | Meade et al. |
| 6,541,617 B1 | 4/2003 | Bamdad et al. |
| 6,600,026 B1 | 7/2003 | Yu |
| 6,686,150 B1 | 2/2004 | Blackburn et al. |
| 6,740,518 B1 | 5/2004 | Duong et al. |
| 6,753,143 B2 | 6/2004 | Tao et al. |
| 6,761,816 B1 | 7/2004 | Blackburn et al. |
| 6,942,771 B1 | 9/2005 | Kayyem |
| 6,977,151 B2 | 12/2005 | Kayyem et al. |
| 7,014,992 B1 | 3/2006 | Kayyem et al. |
| 7,018,523 B2 | 3/2006 | Meade |
| 7,045,285 B1 | 5/2006 | Kayyem et al. |
| 7,056,669 B2 | 6/2006 | Kayyem et al. |
| 7,087,148 B1 | 8/2006 | Blackburn et al. |
| 7,090,804 B2 | 8/2006 | Kayyem et al. |
| 7,125,668 B2 | 10/2006 | Kayyem et al. |
| 7,160,678 B1 | 1/2007 | Kayyem et al. |
| 7,172,897 B2 | 2/2007 | Blackburn et al. |
| 7,267,939 B2 | 9/2007 | Meade |
| 7,312,087 B2 | 12/2007 | Duong et al. |
| 7,381,525 B1 | 6/2008 | Kayyem et al. |
| 7,534,331 B2 | 5/2009 | Kayyem |
| 7,560,237 B2 | 7/2009 | O'Connor et al. |
| 7,601,107 B2 | 10/2009 | O'Connor et al. |
| 2001/0034033 A1 | 10/2001 | Meade et al. |
| 2002/0177135 A1 | 11/2002 | Doung et al. |
| 2003/0170677 A1 | 9/2003 | Meade et al. |
| 2003/0232354 A1 | 12/2003 | Yu et al. |
| 2004/0053290 A1 | 3/2004 | Terbrueggen et al. |
| 2004/0101890 A1 | 5/2004 | Meade et al. |
| 2004/0146909 A1 | 7/2004 | Duong et al. |
| 2005/0003398 A1 | 1/2005 | Tao et al. |
| 2005/0003399 A1 | 1/2005 | Blackburn et al. |

FOREIGN PATENT DOCUMENTS

| | | |
|---|---|---|
| WO | WO 93/22678 | 11/1993 |
| WO | WO 97/44651 | 11/1997 |

OTHER PUBLICATIONS

Ahlers et al., "Protein Interactions with Ordered Lipid Films: Specific and Unspecific Binding," *Advanced Materials*, 3:39-46 (1991).

Aizawa et al., "Integrated molecular systems for biosensors," *Sensors and Actuators*, B 24-25:1-5 (1995).

Albers et al., "Design of novel molecular wires for realizing long-distance electron transfer," *Bioelectrochemistry and Bioenergetics*, 42:25-33 (1997).

Anderson et al., "Modified Electrodes," *Anal. Chem.*, 68(12):379R, 404R-422R, 437R-442R, (Jun. 15, 1996).

Arkin et al., "Rates of DNA-Mediated Electron Transfer Between Metallointercalators," *Science*, 273:475-480 (Jul. 26, 1996).

Bain et al., "Formation of Manslayer Films by the Spontaneous Assembly of Organic Thiols from Solution onto Gold," *J. Am. Chem. Soc.* 111:321-335 (1989).

Bain et al., "Formation of Monolayers by the Coadsorption of Thiols on Gold: Variation in the Head Froup, Tail Group, and Solvent," *J. Am. Chem. Soc.* 111:7155-7164 (1989).

Berggren et al., "Capacitance Measurement of Antibody-Antigen Interactions in a Flow System," *Anal. Chem.* 69(18):3651-3657 (Sep. 15, 1997).

Bilewicz et al., "Monomolecular Langmuir-Blodgett Films at Electrodes. Electrochemistry at Single Molecule 'Gate Sites'," *Langmuir*, 11(6):2256-2266 (1995).

Blonder et al., "Application of Redox Enzymes for Probing the Antigen-Antibody Association at Monolayer Interfaces: Development of Amperometric Immunosensor Electrodes," *Anal. Chem.*, 68(18):3151-3157 (Sep. 15, 1996).

Brewster e al., "Immunoelectrochemical Assays for Bacteria: Use of Epifluorescence Microscopy and Rapid-Scan Electrochemical Techniques in Development of an Assay for Salmonella," *Anal. Chem.*, 68 (23):4153-4159 (Dec. 1, 1996).

Brown et al., "Metalloorganic labels for DNA sequencing and mapping," *New J. Chem.*, 18:317-326 (1994).

Cai et al., "Electrochemical analysis of formation of polynucleotide complexes in solution and at electrode surfaces," *Analytica Chimica Acta*, 344:65-76 (1997).

Carter et al., "Electrochemical Investigations of the Interaction of Metal Chelates with DNA. 3. Electrogenerated Chemiluminescent Investigation of the Interaction of Tris (1,10-phenanthroline) ruthenium (II) with DNA," *Bioconjugate Chem.*, 1 (4):257-263 (1990).

Carter et al., "Oxidation of DNA and RNA by Oxoruthenium(IV) Metallointercalators: Visualizing the Recognition Properties of Dipridophenazine by High-Resolution Electrophoresis," *J. Am. Chem. Soc.*, 120(4):632-642 (1998).

Carter et al., "Oxidation of DNA Hairpins by Oxoruthenium(IV): Effects of Sterics and Secondary Structure," *Inorg. Chem.*, 35(11):3348-3354 (1996).

Chailapakul et al., "Interactions between Organized, Surface-Confined Monolayers and Liquid-Phase Probe Molecules. 4. Synthesis and Characterization of Nanoporous Molecular Assemblies: Mechanism of Probe Penetration," *Langmuir*, 11(4):1329-1340 (1995).

Charych et al., "Direct Colorimetric Detection of a Receptor-Ligand Interaction by a Polymerized Bilayer Assembly," *Science*, 261:585-588 (Jul. 30, 1993).

Cheng et al., "Selectivity and Sensitivity of Self-Assembled Thioctic Acid Electrodes," *Anal. Chem.*, 64(17):1998-1999 (Sep. 1, 1992).

Cornell et al., "A biosensor that uses ion-channel switches," *Nature*, 387:580-583 (Jun. 5, 1997).

Cullison et al., "Cyclic Voltammetry with Harmonic Lock-In Detection: Applications to Flow Streams," *Electoanalysis*, 8(4):314-319 (1996).

Cygan et al., "Insertion, Conductivity, and Structures of Conjugated Organic Oligomers in Self-Assembled Alkanethiol Monolayers on Au {111}," 120(12):27212732 (1998).

Delamarche et al., "Immobilization of Antibodies on a Photoactive Self-Assembled Monolayer on Gold," *Langmuir*, 12:1997-2006 (1996).

Dhirani et al., "Self-Assembly of Conjugated Molecular Rods: A High Resolution STM Study," *J. Am. Chem. Soc.*, 118(13):3319-3320 (1996).

Dong et al., "Characteristics of the glucose oxidase at different surfaces," *Biochemistry and Bioenergetics*, 42:63-69 (1997).

Dong et al., "Self-assembled monolayers of thiols on gold electrodes for bioelectrochemistry and biosensors," *Biochemistry and Bioenergetics*, 42:7-13 (1997).

Doron et al., "An Electroative Photoisomerizable Monolayer-Electrode: A Command Surface for the Amperometric Trnsduction of Recorded Optical Signals," *Angew. Chem. Int. Ed. Engl.*, 35(13/14):1535-1538 (1996).

Duan et al., "Immobilizationof Proteins on Gold Coated Porous Membranes Via an Activated Self-Assembled Monolayer of Thiotic Acid," *Mikrochim. Acta.*, 117:195-206 (1995).

Duan et al., "Separation-Free Sandwich Enzyme Immunoassays Using Microporous Gold Electrodes and Self-Assmebled Monolayer/Immobilized Capture Antibodies," *Anal. Chem.*, 66(9):1369-1377 (May 1, 1994).

Ducey et al., "Competitive nonseparation electrochemical enzyme binding/immunoassay (NEEIA) for small molecule detection," *Analytical Chimica Acta.*, 357:5-12 (1997).

Ewing, A., et al., "Electrochemical detection in microcolumn separations," *Anal. Chem.* 66(9):527A-537A (May 1994).

Feng et al., "A self-assembled antibody electrode for HT29 tumour cells," *Biotechnol. Appl. Biochem.*, 26:163-167 (1997).

Fojta et al., "Supercoiled DNA-modified mercury electrode: A highly sensitive tool for the detectiono f DNA damage," *Analytica Chimica Acta*, 342:1-12 (1997).

Fukui et al., "Distance Dependence of Photoinduced Electron Transfer in DNA," *Angew. Chem. Int. Ed.*37(1/2):158-161 (1998).

Gafni et al., "Biomimetic Ion-Binding Monolayers on Gold and Their Characterization by AC-Impedance Spectroscopy," *Chem. Eur. J.*, 2(7):759-766 (1996).

Gafni et al., Biomimetic Ion-Binding Monolayers on Gold and Their Characterization by AC-Impedance Spectroscopy, *Chem. Eur. J.*, 1996, 2, No. 7, pp. 759-766.

Gardner, J., et al., "Application of conducting polymer technology in Microsystems," *Sens. Actuators* A 51:57-66 (1995).

Gasper et al., "Intramolecular Photoinduced Electron Transfer to Anthraquinones Linked to Duplex DNA: The Effect of Gaps and Traps on Long-Range Radical Cation Migration," *J. Am. Chem. Soc.*, 119(52):12762-12771 (1997).

Ghindilis et al., "Immunosensors: electrochemical sensing and other engineering approaches," *Biosensors & Bioelectronics*, 13(1):113-131 (1998).

Hall et al., "Sensitivity of DNA-Mediated Electron Transfer to the Intervening .pi.-Stack: A Probe for the Integrity of the DNA Base Stack," *J. Am. Chem. Soc.*, 119(21):5045-5046 (1997).

Harrison et al., "Characterization of Perfluorosulfonic Acid Polymer Coated Enzyme Electrodes and a Miniaturized Integrated Potentiostat for Glucose Analysis in Whole Blood," *Anal. Chem.*, 60(19):2002-2007 (1988).

Hashimoto et al., "Novel DNA sensor for electrochemical gene detection," *Analytica Chimica Acta*, 286:219-224 (1994).

Hashimoto et al., "Sequence-Specific Gene Detection with a Gold Electrode Modified with DNA Probes and an Electrochemically Active Dye," Analytical Chemistry, 66(21):3830-3833 (Nov. 1, 1994).

Haussling et al., "Biotin-Functionalized Self-Assembled Monolayers on Gold: Surface Plasmon Optical Studies of Specific Recognition Reactions," *Langmuir*, 7(9):1837-1840 (Sep. 1991).

Haussling et al., "Direct Observation of Streptavidin Specifically Adbsorbed on Biotin-Functionalized Self-Assembled Monolayers with Scanning Tunneling Microscope," *Angew. Chem. Int. Ed. Engl.* 30, 5:569-572 (1991).

Henke et al., "Self-Assembled Monolayers of Monofunctionalized Cyclodextrins onto Gold: A Mass Sepctrometric Characterization and Impedance Analysis of Host-Guest Interaction," *Analytical Chemistry*, 68(18):3158-3165 (Sep. 15, 1996).

Holmlin et al., "Charge Transfer through the DNA Base Stack," *Angew. Chem. Int. Ed. Engl.*, 36:2714-2730 (1997).

Hsung et al., "Thiophenol Protecting Groups for the Palladium-Catalyzed Heck Reaction: Efficient Syntheses of Conjugated Arylthiols," *Tetrahedron Letters*, 36(26):4525-2528 (1995).

Hsung et al., Synthesis and Characterization of Unsymmetric FerroceneTerminated Phenylethynyl Oligomers $CP_2FE[C=C-C_6H_4]_n$ -X (X=SH, SM, SOMe, and $SO_2ME$), *Organometallics*, 14(10):4808-4815 (1995).

Ihara et al., "Gene sensor using ferrocenyl oligonucleotide," *Chem. Commun.*, 1609-1610 (1997).

Jiang et al., "Characterising the formation of a bioelectrochemical interface at a self-assembled monolayer using X-ray photoelectron spectroscopy," *Biochemistry and Bioenergetics*, 42:15-23 (1997).

Jiang et al., "Direct Electron Transfer Reactions of Glucose Oxidase Immobilised at a Self-assembled Monolayer," *J. Chem. Soc., Chem. Commun.*, 1293-1295 (1995).

Johnston et al., "Cyclic Voltammetry of Polynucleotide Binding and Oxidation by Metal Complexes Homogeneous Electron-Transfer Kinetics," *J. Phys. Chem.*, 100(32):13837-13843 (1996).

Johnston et al., "Trans-Dioxorhenium(V)-Mediated Electrocatalytic Oxidation of DNA at Indium Tin-Oxide Electrodes: Voltammetric Detection of DNA Cleavage in Solution," *Inorganic Chemistry*, 33(26):6388-6390 (1994).

Ju et al., "Host-Guest Interaction at a Self-Assembled Monolayer/Solution Interface: An Electrochemical Analysis of the Inclusion of 11- (Ferrocenylcarbonyloxy) undecanethiol by Cyclodextrins," *Langmuir*, 14:300-306 (1998).

Kaifer et al., "Functionalized Self-Assembled Monolayers Containing Preformed Binding Sites," *Israel Journal of Chemistry*, 36:389-397 (1996).

Katz et al., "Application of stilbene-(4,4'-diisothiocyanate)-2,2'-disulfonic acid as a bifunctional reagent for the organization of organic materials and proteins onto electrode surfaces," *J. Electroanal. Chem.*, 354:129-144 (1993).

Katz et al., "Electrical contact of redox enzymes with electrodes: novel approaches for amperometric biosensors," *Biochemistry and Bioenergetics*, 42:95104 (1997).

Katz et al., "Electron Transfer in Self-Assembled Monolayers of N-Methyl-N'- carboxyalkyl-4,4'-bipyridinium Linked to Gold Electrodes," *Langmuir* 9:1392-1396 (1993).

Kaxiras, Materials Research Society Symposium Proceedings, 1990, 193 (At. Scale Calc. Structure. Mater.), 143-148--Abstract Only.

Kelley et al., "Electrochemistry of Methylene Blue Bond to a DNA-Modified Electrode," *Bioconjugate Chem.* 8(1):31-37 (1997).

Kelley et al., "Photoinduced Electron Transfer in Ethidium-Modified DNA Duplexes: Dependence on Distance and Base Stacking," *J. Am. Chem. Soc.*, 119(41):9861-9870 (1997).

Knichel et al., "Utilization of a self-assembled peptide monolayer for an impedimetric immunosensor," *Sensors and Acuators*, B 28:85-94 (1995).

Kunitake et al., "'Interfacial Buffer Effect' of Self-assembled Monolayers of a Carboxylic Acid Terminated Alkanethiol of a Gold Electrode," *J. Chem. Soc., Chem. Commun.*, 563-564 (1994).

Kunitake et al., "Transmembrane Rectified Electron Transfer through .pi.-Conjugated Electroactive Langmuir-Blodgett Monolayers on Gold Electrodes," *Bull. Chem. Soc. Jpn.*, 67(2)373-378 (1994).

Li et al., "Viologen-thiol self-assembled monolayers for immobilized horseradish peroxidase at gold electrode surface," *Electrochimica Acta*, 42(6):961-967 (1997).

Liedberg et al:, "Self-Assembly of .alpha.-Functionalized Terthiophenes on Gold," *J. Phys. Chem. B.*, 101(31):5951-5962 (1997).

Lindholm-Sethson, B., "Electrochemistry at Ultrathin Organic Films at Planar Gold Electrodes," *Langmuir*, 12(13):3305-3314 (1996).

Lion-Dagan et al., "A Bifunctional Monolayer Electrode consisting of 4-Pyridyl Sulfide and Photoisomerizable Spiropyran: Photoswitchable Electrical Communication between the Electrode and Cytochrome C," *J. Chem. Soc., Chem. Commun.*, 2741-2742 (1994).

Liu et al., "Voltammetric determination of sequence-specific DNA by electroactive intercalator on graphite electrode," *Analytica Chimica Acta*, 335:239-243 (1996).

Lotzbeyer et al., "Minizymes. A new strategy for the development of reagentless amperometric biosensors based on direct electron-transfer process," *Biochemistry and Bioenergetics*, 42:1-6 (1997).

Maeda et al., "$Mg.sup.2+$-Selective Electrode Comprising Double-Helical DNA as Receptive Entity," Chemistry Letters, 1805-1808 (1994).

Malem et al., "Self-Assembled Monolayers in Electroanalytical Chemistry: Application of .omega.-Mercaptocarboxylic Acid Monolayers for Electrochemical Detection of Dopamine in the Presence of a High Concentration of Absorbic Acid," *Anal. Chem.*, 66(1):37-41 (Jan. 1, 1993).

Mandler et al., "Applications of Self-Assembled Monolayers in Electroanalytical Chemistry," *Electranalysis*, 8(3):207-213 (1996)95).

Michalitsch et al., Properties of Self-Assembled Monolayers (SAMs) from Thiol-Functionalized Oligothiophenes, *Adv. Mater.*, 9(4):31-325 (1997).

Naumann et al., "Incorporation of Membrane Proteins in Solid-Supported Lipid Layers," *Angew. Chem. Int. Ed. Eng.*, 34(18):2056-2058 (1995).

Nejdarkova et al., "Glucose minisensor based on self-assembled biotinylated phospholipid membrane on a solid support and its physical properties," *Biochemistry and Bioenergetics*, 42:35-42 (1997).

Nejdarkova et al., "Design of a Glucose Minisensor Based on Streptavidin-Glucose Oxidase Complex Coupling with Self-Assembled Biotinylated Phospholipid Membrane on Solid Support," *Anal. Chem.*, 65(6):665-668 (1993).

Nikoleilis et al., "Ammonium Ion Minisensors from Self-Assembled Bilayer Lipid Membranes Using Gramicidin as an Ionophore. Modulation of Ammonium Selectivity by Platelet-Activating Factor," *Analytical Chemistry*, 68(10):1735-1741 (May 15, 1996).

Niwa et al., "Specific Binding of Concanavalin a to Glycolipid Monolayers on Gold Electrodes," *J. Chem. Soc., Chem. Commun.* 547-549 (1992).

Nuzzo et al., "Adsorption of Bifunctional Organic Disulfides on Gold Surfaces," *J. Am. Chem. Soc.* 105(15):4481-4483 (1983).

Ohno, Surface Science, 1991, 255(3), 229-236--Abstract Only.

Paleck et al., "Differential Pulse Voltammetric Determination of RNA at the Picomole Level in the Presence of DNA and Nucleic Acid Components," *Anal. Chem.*, 66(9):1566-1571 (May 1, 1994).

Pang et al., "Modification of glassy carbon and gold electrodes with DNA," *Journal of Electroanalytical Chemistry*, 403:183-188 (1996).

Reed et al., "Conductance of a Molecular Junction," *Science*, 278:252-254, (Oct. 10, 1997).

Rickert et al., "A 'mixed' self-assembled monolayer for an impedimetric immunosensor," *Biosensors & Bioelectrics*, 11(8):757-768 (1996).

Mikkelsen, S., "Electrochemical Biosensors for DNA Sequence Detection," *Electroanalysts*, 8(1):15-19 (1996).

Millan et al., "Sequence-Selective Biosensor for DNA Based Electroactive Hybridzation Indicators," *Analytical Chemistry*, 65(17):2317-2323 (Sep. 1, 1993).

Millan et al., "Voltammetric DNA Biosensor for Cystic Fibrosis Based on a Modified Carbon Paste Electrode," *Analytical Chemistry*, 66(18):2943-2948 (Sep. 15, 1994).

Mirkhalaf et al., "Surface spectroscopy and electrochemical characterisation of metal dithizonates covalently attached to gold by a self-assembled cysteamine monolayer," *J. Chem. Soc., Faraday Trans.*, 94(9):1321-1327 (1998).

Moore et al., "Cation Recognition by Self-Assembled Layers of Novel Crown-Annelated Tetrathiafulvalenes," *Advance Materials*, 10(5):395-398 (1998).

Motesharei et al., "Diffusion-Limited Size-Selective Ion Sensing Based on SAM-Supported Peptides Nanotubes," *J. Am. Chem. Soc.*, 119(40):11306-11312 (1997).

Mucic et al., "Synthesis and charactrization of DNA with ferrocenyl groups attached to their 5'-termini: electochemical characterization of a redox-active nucleotide monolayer," *Chem. Commun.*, 555-557 (1996).

Nakashima et al., "An Ion Gate Lipid Monolayer Membrane on Gold Electrodes," *J. Chem. Soc., Chem. Comm.*, 232-233 (1991).

Nakashima, N., "Functionalized of metal electrode surfaces with monolayers, bilayers and LB films."

Napier et al., "Modification of Electrodes with Dicarboxylate Self-Assembled Monolayers for Attachment and Detection of Nucleic Acids," *Langmuir*, 13(23):6342-6344 (1997).

Napier et al., "Probing Biomolecule Recognition with Electron Tranfer: Electrochemical Sensors for DNA Hybridization," *Bioconjugate Chem.*, 8(6):906913 (1997).

Rickert et al., "Self-assembled monolayers for chemical sensors: molecular Recognition by immobilized supramolecular structures," *Sensors and Actuatos, B*31:45-50 (1996).

Rojas et al., "Molecular Recognition at the Electrode-Solution Interface, Design, Self-Assembly, and Interfacial Binding Properties of a Molecular Sensor," *J. Am. Chem. Soc.*, 117(21):5883-5884 (1995).

Rubin et al., "Electrical Communication between Components of Self-Assembled Mixed Monolayers," *Langmuir*, 12:363-370 (Nov. 12, 1996).

Rubinstein et al., "Ionic recognition and selective response in self-assembling monolayer membranes on electrodes," *Nature*, 332:426-429 (Mar. 31, 1988).

Sabatani et al., "Thioaromatic Monolayers on Gold: A New Family of Self-Assembling Monolayers," *Langmuir*, 9(11):2974-2981 (1993).

Sachs et al., "Rates of Interfacial Electron Transfer through Conjugated Spacers," *J. Am. Chem. Soc.*, 119(43):10563-10564 (1997).

Sakamotoa et al., "Design and synthesis of flavin-conjugated peptides and assembly on a gold electrode," J. Chem. Soc., Perkin Trans., 2:2319-2326 (1996).

Schierbaum et al., "Molecular Recognition by Self-Assembled Monolayers of Cavitand Receptors," *Science*, 265:1413-1415 (Sep. 2, 1994).

Schlereth et al., "Self-assembled monolayers with biospecific affinity for lactate dehydrogenase for the electroenzymatic oxidation of lactate," *Journal of Electroanalytical Chemistry*, 431:285-295 (1997).

Schumann et al., "Immobilization of Enzymes on Langmuir-Blodgett Films via a Membrane-Bound Receptor, Possible Applications for Amperometric Biosensors," *Adv. Mater.*, 7/8:388-391 (1991).

Singhal et al., "Sinusoidal Voltammetry for the Analysis of Carbohydrates at Copper Electrodes," *Analytical Chemistry* 69(8):1662-1668 (Apr. 15, 1997).

Singhal et al., "Ultrasensitive Voltammetic Detection of Underivatized . Oligonucleotides and DNA," *Anal. Chem.*, 69(23):4828-4832 (1997).

Singhal. et al., "Direct Electrochemical Detection of Purine- and Pyrimidine-Based Nucleotides with Sinusoidal Voltammetry," *Analytical Chemistry*, 69(17):3552-3557 (Sep. 1, 1997).

Skladal, P., "Advances in Electrochemical Immunosensors," *Electroanalysis*, 9(10):737-745 (1997).

Smalley et al., "Kinetics of Electron Transfer through Ferrocene-Terminated Alkanethiol Monolayers Gold," *J. Phys. Chem.*, 99(35):13141-13149 (1995).

Souteyrand et al., "Direct Detection of the Hybridization of Synthetic Homo-Oligomer DNA Sequences by Field Effect," *J. Phys. Chem. B.*, 101(15):2980-2985 (1997).

Spinke et al., "Molecular recognition at self-assembled monolayers: Optimization of surface functionalization," *J. Chem. Phys.*, 99(9):7012-7019 (Nov. 1, 1993).

Steinbeck et al., "Model systems for molecular recognition at interfaces: synthesis and characterisation of functionalized disulfides with hydrogen-bonding properties," *Chem. Commun.*, 1193-1194 (1996).

Steinberg et al., "Ion-Selective Monolayer Membranes Based upon Self-Assembling Tetradentate Ligand Monolayers on Gold Electrodes. 2. Effect of Applied Potential on Ion Binding," *J. Am. Chem. Soc.* 113:5176-5182 (1991).

Steinberg et al., "Ion-Selective Monolayer Membranes Based upon Self-Assembling Tetradentate Ligand Monolayers on Gold Electrodes. 3. Application as Selective Ion Sensors," *Langmuir*, 8(4):1183-1187 (1992).

Steinem et al., "Impedance analysis of supported lipid bilayer membranes: a scrutiny of different preparation techniques," *Biochimica et Biophysica Acta*, 1279:169-180 (1996).

Stelzle et al., "On the Application of Supported Bilayers as Receptive Layers for Biosensors with Electrical Detection," *J. Phys. Chem.*, 97(12):2974-2981 (1993).

Stora et al., "Metal Ion Trace Detection by a Chelator-Modified Gold Electrode: a Comparison of Surface to Bulk Affinity," *Langmuir*, 13(20):5211-5214 (Oct. 1, 1997).

Sun et al., "Preparation of Active Langmuir-Blodgett Films of Glucose Oxidase," *Langmuir*, 7(4):727-737 (1991).

Takehara et al., "An Ion-Gate Response of a Glutathione Monolayer Assembly Highly Sensitive to Lanthanide Ions," *Electroanalysis*, 6:1083-1086 (1994).

Takehara et al., "An ion-gate response of the cysteine-containing dipeptide monolayers formed on a gold electrode. The effects of alkaline earth ions," *Biochemistry and Bioenergetics*, 39:135-138 (1996).

Takehara et al., "Charge-selectivity of the monolayer modified gold electrode for the electrochemical oxidationof catechol derivatives," *Journal of Electroanalytical Chemistry*, 404:179-182 (1996).

Takehara et al., "Electrochemical behavior of ubiquinone and vitamin K incorporated into n-alkanethiol molecular assemblies on a gold electrode," *J. Electroanal. Chem.*, 308:345-350 (1991).

Takenaka et al., "Electrochemically Active DNA Probes: Detection of Target DNA Sequences at Femtomole Level by High-Performance Liquid Chromatography with Electrochemical Detection," *Analytical Biochemistry*, 218:436-443 (1994).

Terrettaz et al., "Protein Binding to Supported Lipid Membranes: Investigation of the Cholera Toxin-Ganglioside Interaction by Simultaneous Impedance Spectroscopy and Surface Plasmon Resonance," *Langmuir*, 9(5):1361-1369 (1993).

Thorp et. al., "Cutting out the middleman: DNA biosensors based on electrochemical oxidation," *TIBTECH*, 16 (Mar. 1998).

Tien et al., "Electrochemistry of supported bilayer lipid membranes: background and techniques for biosensor development," *Biochemistry and Bioenergetics*, 42:77- 94 (1997).

Tominaga et al., "Tuning of lipid bilayer fluidity regulates mediated electron transfer reactions of glucase oxidase immbolized on lipid bilayer films on an electrode," *Biochemistry and Bioenergetics*, 42:59-62 (1997).

Tour et al., "Self-Assembled Monolayers and Multilayers of Conjugated Thiols, .alpha..omega.-Diothiols, and Thioacetyl-Containing Adsorbates. Understanding Attachments between Potential Molecular Wires and Gold Surfaces," *J. Am. Chem. Soc.*, 117(37):9539-9534 (1995).

Turro et al., "Molecular Recognition and Chemistry in Restricted Reaction Spaces. Photophysis and Photophysics and Photoinduced Electron Transfer on the Surfaces of Micelles, Dendrimers, and DNA," *Acc. Chem. Res.*, 24(11):332-340 (1991).

Turyan et al., "Selective Determination of Cr(VI) by a Self-Assembled Monolayer-Based Electrode," *Analytical Chemistry*, 69(5):894-897 (Mar. 1, 1997).

Turyan et al., "Self-Assembled Monolayers in Electroanalytical Chemistry: Application of .omega.-Mercaptocarboxylic Acid Monolayers for Electrochemcial Determination of Ultralow Levels of Cadmium," *Analytical Chemistry*, 66(1):58-63 (Jan. 1, 1994).

Wagner et al., "Covalent Immobilization of Native Biomolecules onto Au(111) via N-Hydroxysuccinimide Ester Functionalized Self-Assembled Monolayers for Scanning Probe Microscopy," *Biophysical Journal*, 70:2052-2066 (May 1996).

Wang et al., "Adsorptive Stripping Potentiometry of DNA at Electrochemically Pretreated Carbon Paste Electrodes," *Electroanalysts*, 8(1):20-24 (1996).

Wang et al., "DNA Biosensor for the Detection of Hydrazines," *Analytical Chemistry*, 68(13):2251-2254 (Jul. 1, 1996).

Wang et al., "DNA Electrochemical Biosensor for the Detection of Short DNA Sequences Related to the Human Immunodeficiency Virus," *Analytical Chemistry*, 68(15)2629-2635 (Aug. 1, 1996).

Wang et al., "Peptide Nucleic Acid Probes for Sequence-Specific DNA Biosensors," *J. Am. Chem. Soc.*, 118(33):7667-7670 (1996).

Wang et al., "Stripping potentiometric transductionof DNA hybridization processes," *Analytica Chimica Acta*, 326:141-147 (1996).

Wang, J., "Electroanalysis and Biosensors," *Anal. Chem.*, 67(12):487R-492R (Jun. 15, 1995).

Wang, J.,-"Electroanalysis and Bionsensors," *Anal. Chem.*, 69(12):165R-166R, 184R-187R, 221R-223R (Jun. 15, 1997).

Welch et al., "Distribution of Metal Complexes Bound to DNA Determined by Normal Pulse Voltammetry," *J. Phys. Chem.*, 100(32):13829-13836 (1996).

Welch et al., "Electron-Rich Oxoruthenium(IV) Cleavage Agents: A Zero-Order Rate Law for DNA Catalysis," *Inorg. Chem.*, 36(21):4812-4821 (1997).

Whitesides et al., "Wet Chemical Approaches to the Characterization of Organic Surfaces: Self-Assembled Monolayers, Wetting, and the Physical-Organic Chemistry of the Solid-Liquid Interface," *Langmuir*, 6:87-96 (1990).

Willner et al., "Application of Photoisomerizable Antigenic Monolayer Electrodes as Reversible Amperometric Immunosensors," *J. Am. Chem. Soc.*, 16(20):9365-9366 (1994).

Willner et al., "Assembly of functionalized monolayers of redox proteins on electrode surfaces: novel bioelectronic and optobioelectronic systems," *Biosensors & Bioelectronics*, 12(4):337-356 (1997).

Willner et al., "Development of Novel Biosensor Enzyme Electrodes: Glucse Oxidase Multilayer Arrays Immobilized onto Self-Assembled Monolayers on Electrodes," *Adv. Mater.*, 5(12):912-915 (1993).

Willner et al., "Electrical Communication between Electrodes and NAD(P).sup.+-Dependent Enzymes Using Pyrroloquinolinequinone-Enzyme Electrodes in a Self-Assembled Monolayer Configuration: Design of a New Class of Amperometric Biosensors," *Analytical Chemistry*, 66(9):1535-1539 (May 1, 1994).

Willner et al., "Electron-Transfer Communication between Redox-Functionalized Polymers and the Active Center of the Enzyme Glutathione Reductase," *J. Am. Chem. Soc.*, 114(27):10963-10965 (1992).

Willner et al., "Electron-Transfer Communication in Glutathione Reductase Assemblies: Electrocatalytic, Photocatalytic, and Catalytic Systems for the Reduction of Oxidized Glutatione," *J. Am. Chem. Soc.*, 116(4):1428-1441 (1994).

Willner et al., "Mediated Electron Transfer in Glutathione Reductase Organized in Self-Assembled Monolayers on Au Electrodes," *J. Am. Chem. Soc.*, 114:1096510966 (1992).

Willner et al., "Photoregulated Binding of Spiropyran-Modified Concanavalin A to Monosaccharide-Functionalized Self-Assembled Monolayers on Gold Electrodes," *J. Am. Chem. Soc.*, 115(11):4937-4938 (1993).

Willner et al., "Photoswitchable biomaterials as grounds for optobioelectronic devices," Biochemistry and Bioenergetics, 42:43-57 (1997).

Wink et al., "Self-assembled Monolayers for Biosensors," *Analysts*, 122:43R-50R (Apr. 1997).

Woodyear et al., "Direct Enzyme-Amplified Electrical Recognition of a 30-Base Model Oligonucleotide," *J. Am. Chem. Soc.*, 118:5504-5505 (1996).

Xu et al., "Immobilization and Hybridization of DNA on an Aluminum(III) Alkanebisphosphonate Thin Film with Electrogenerated Chemiluminescent Detection," *J. Am. Chem. Soc.*, 117(9):2627-2631 (1995).

Xu et al., "Immobilization and Hybridization of DNA on an Aluminum(III) Alkanebisphosphonate Thin Film with Electrogenerated Chemiluminescent Detection," *J. Am. Chem. Soc.*, 116(18):8286-8387 (1994).

Yang et al., "Genosensor technology and the detection of interfacial nucleic acid chemistry," *Analytica Chimica Acta*, 346:259-275 (1997).

Zehner et al., "Electrochemical Evaluation and Enhancement via Heterogeneous Exchange of the Passivating Properties and Stability of Self-Assembled Monolayes Derived from the Rigid Rod Arenethiols, $X-C_6H_4-C\equiv C_6H_4-C\equiv C-C_6H_4-SH$ (X=H and F)," *Langmuir*, 13(11):2973-2979 (1997).

Zhao et al., "Mediator-Free Amperometric Determination of Toxic Substances Based on Their Inhibition of Immobilized Horseradish Peroxidase," *Biotechnol. Prog.*, 12(5):703-708 (1996).

\* cited by examiner

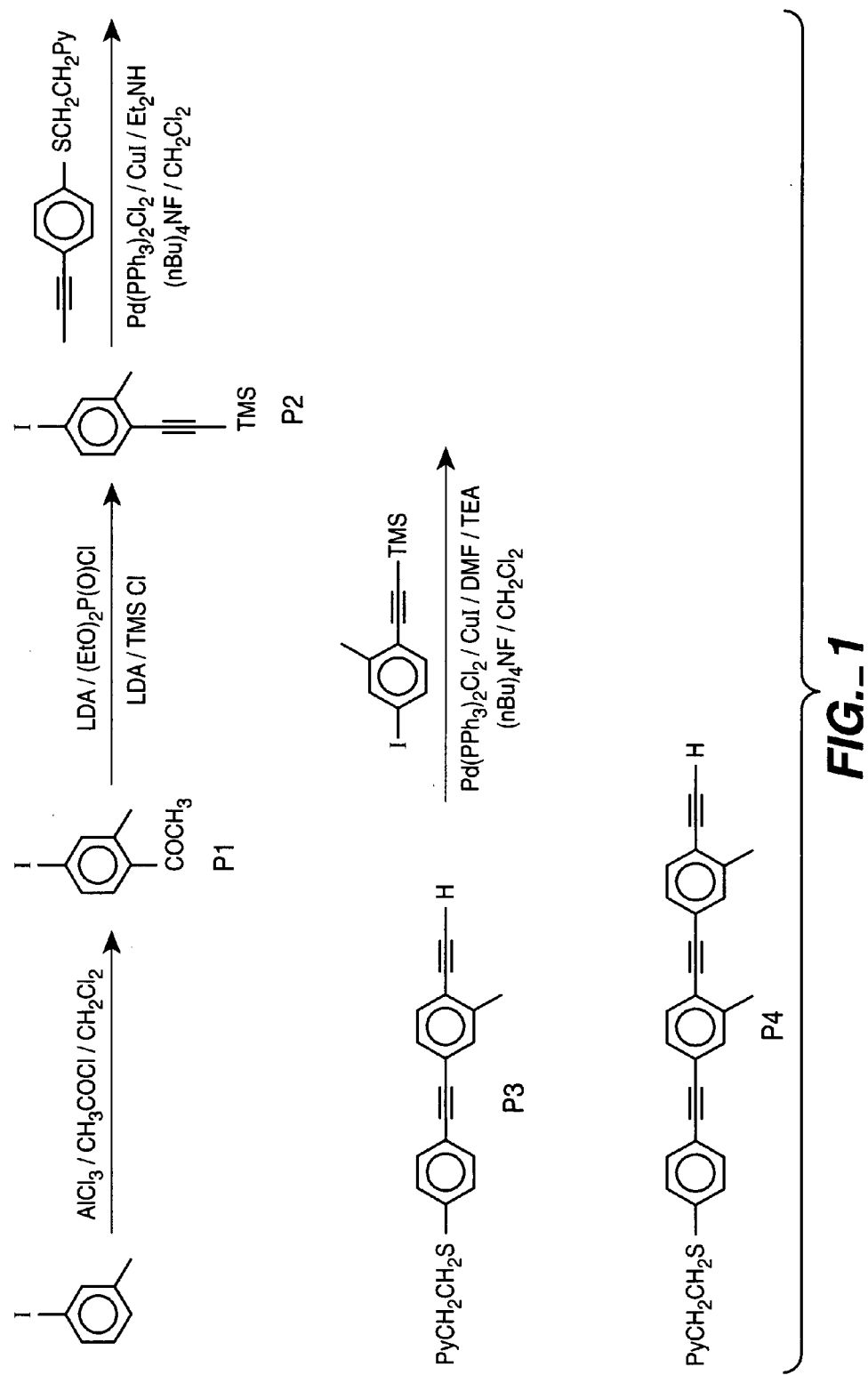
FIG._1

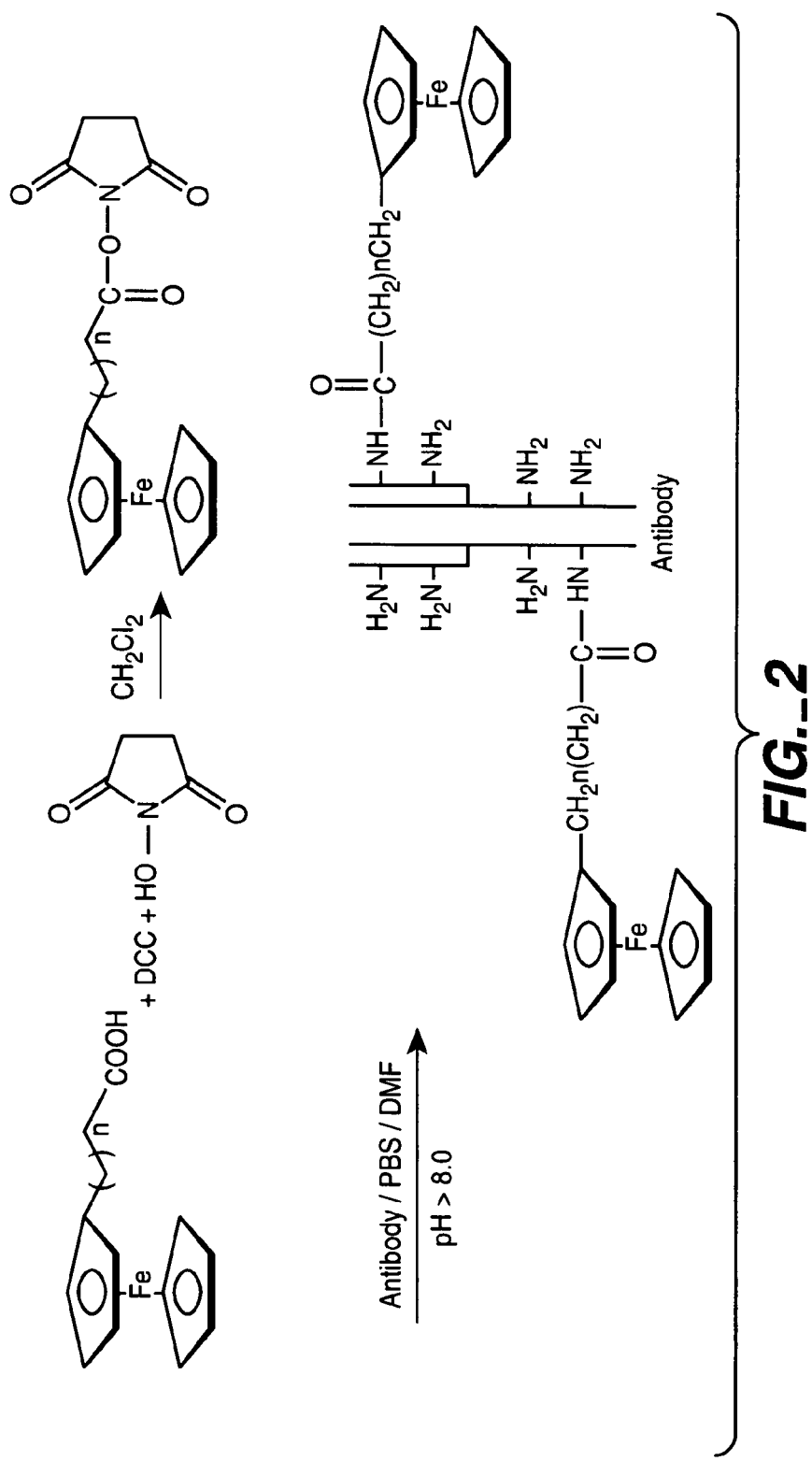
FIG._2

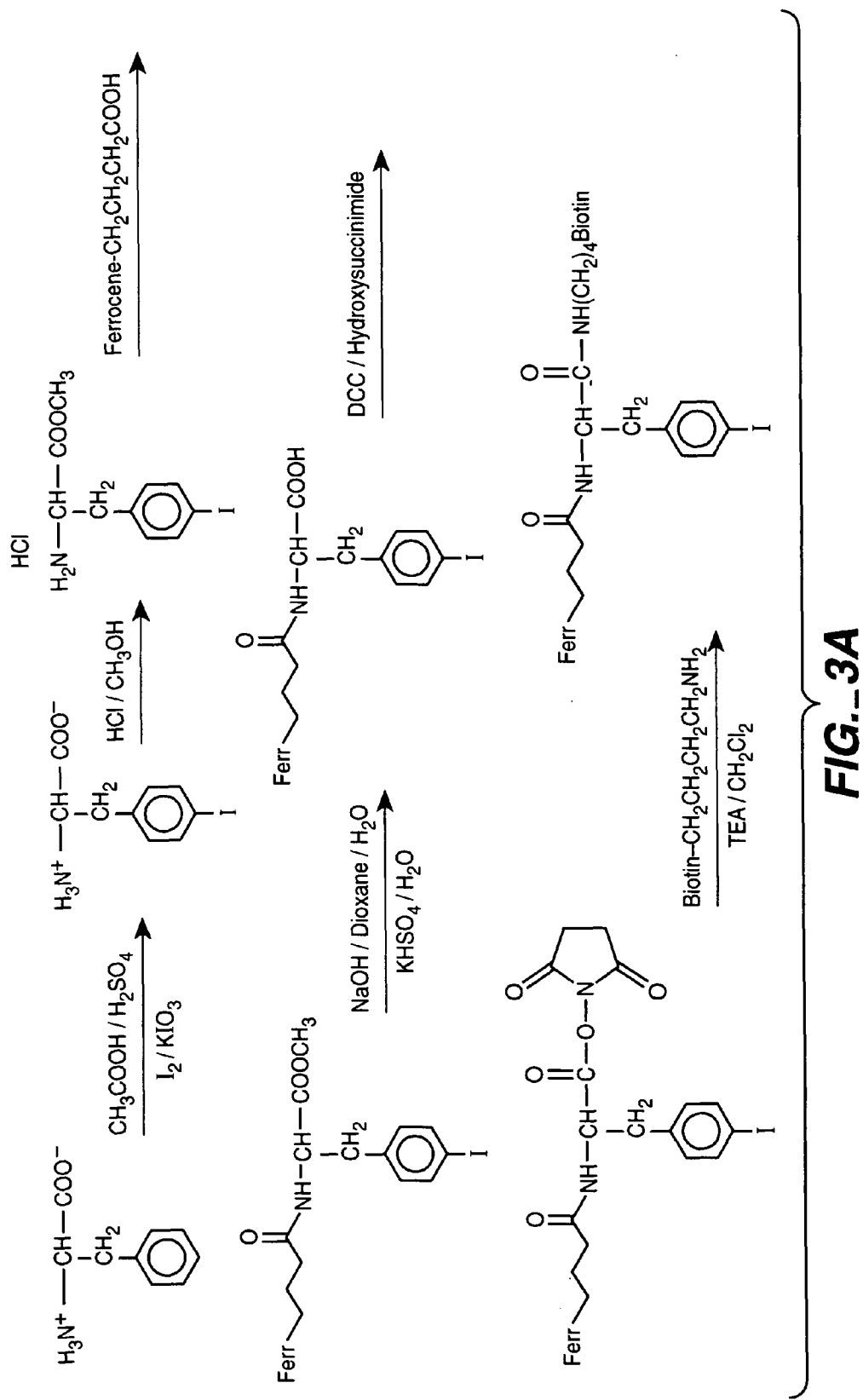
FIG._3A

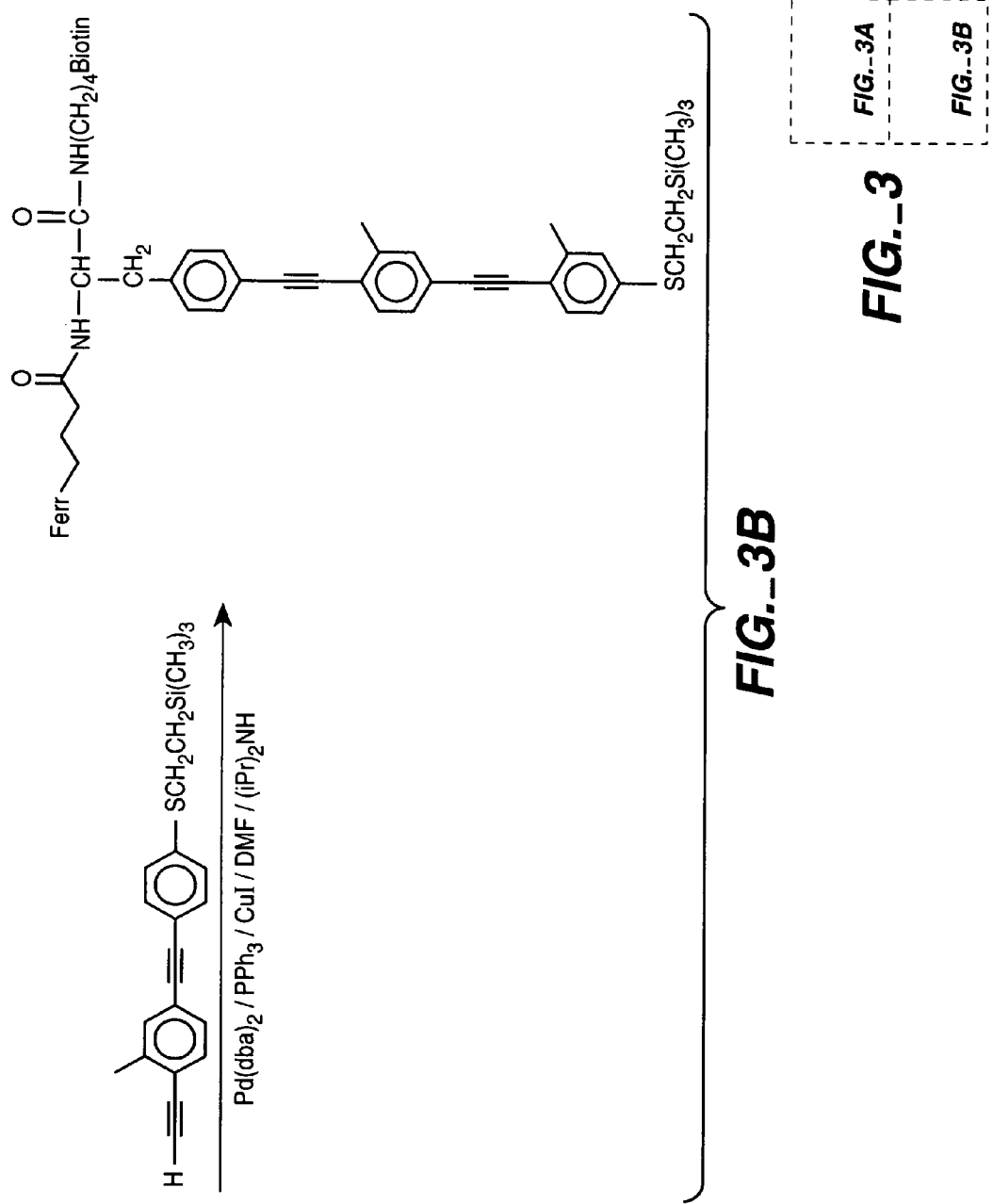
FIG._3B
FIG._3
FIG._3A
FIG._3B

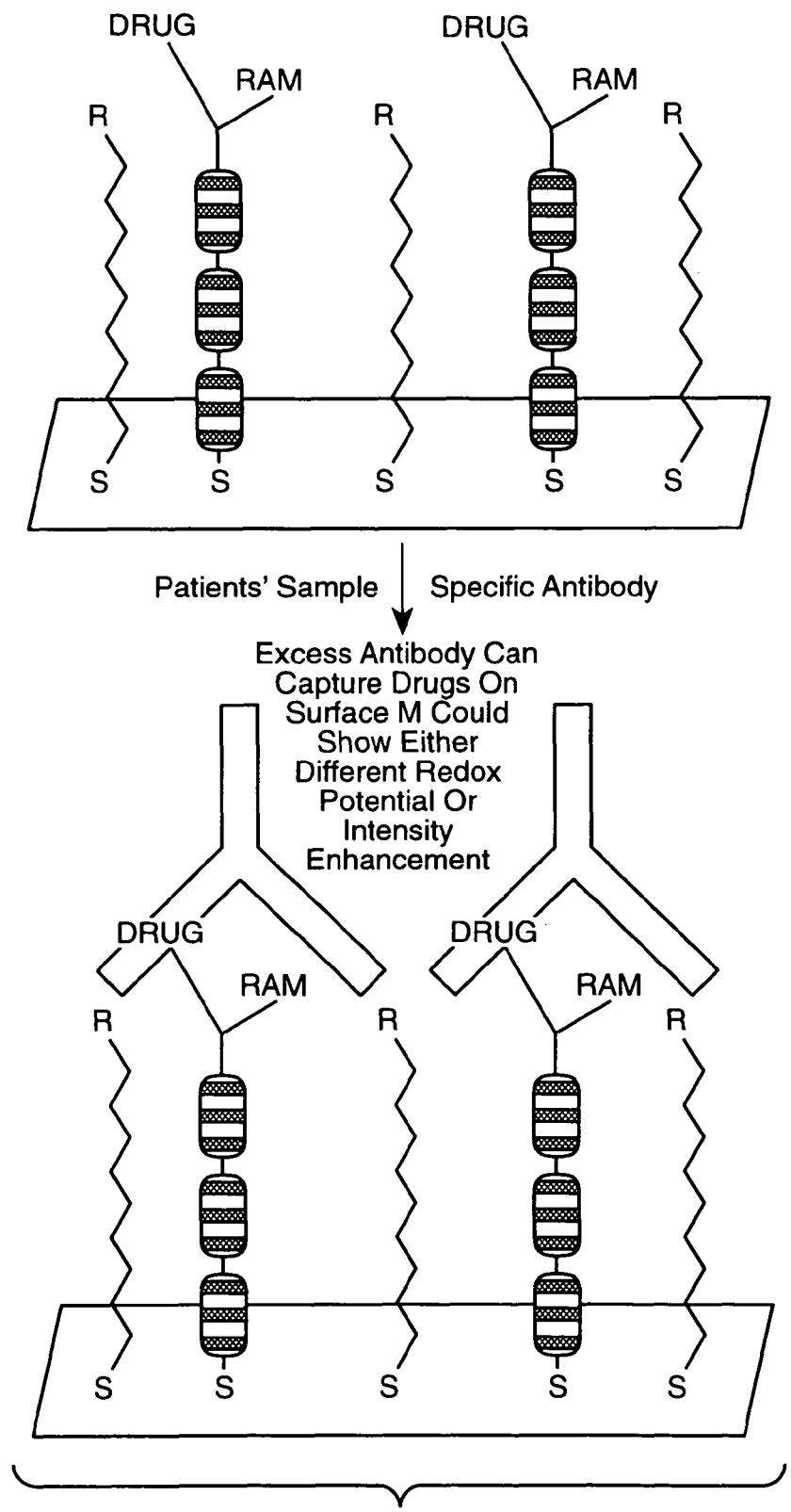
FIG._4

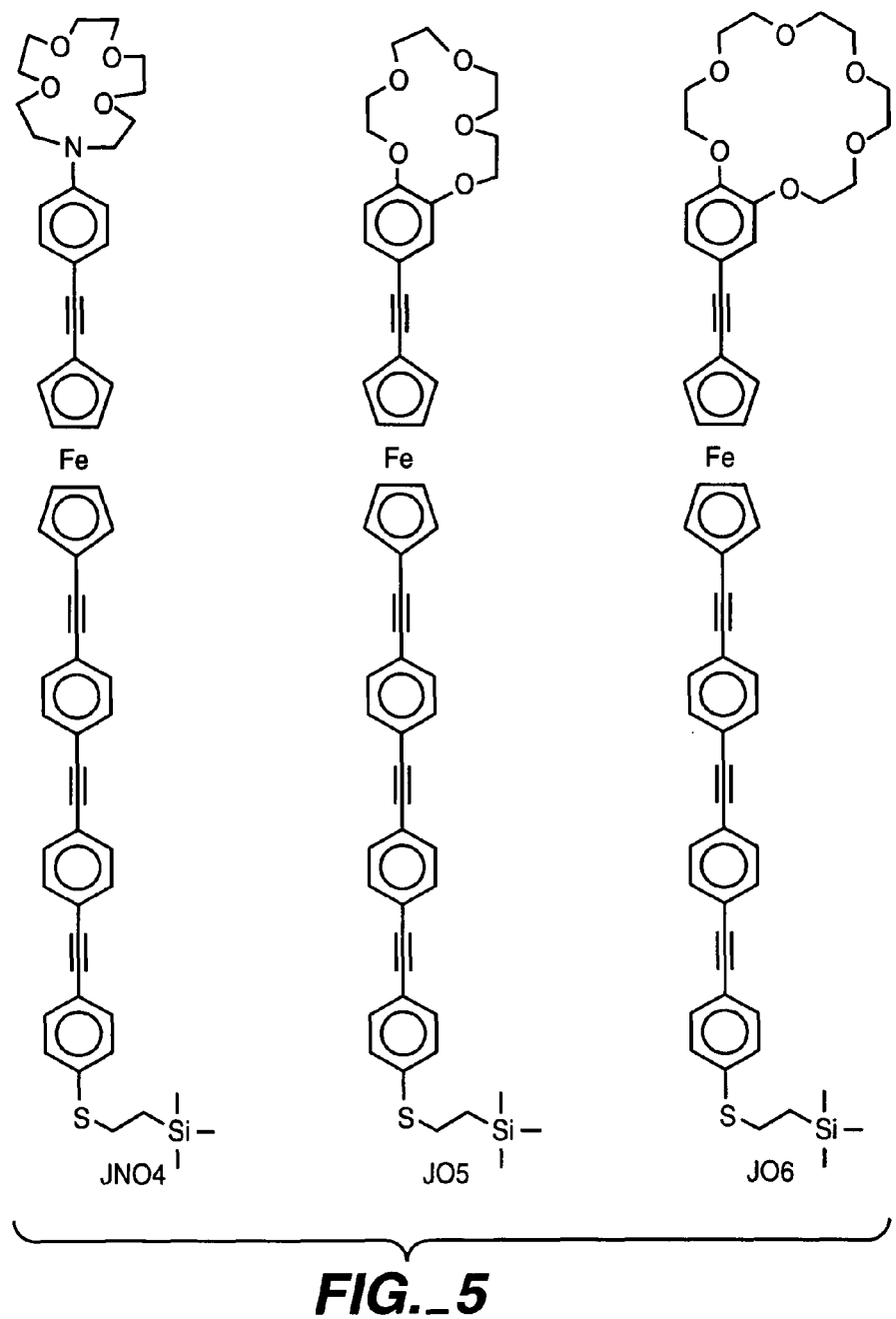
FIG._5
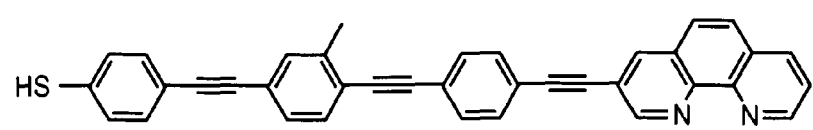
FIG._6A

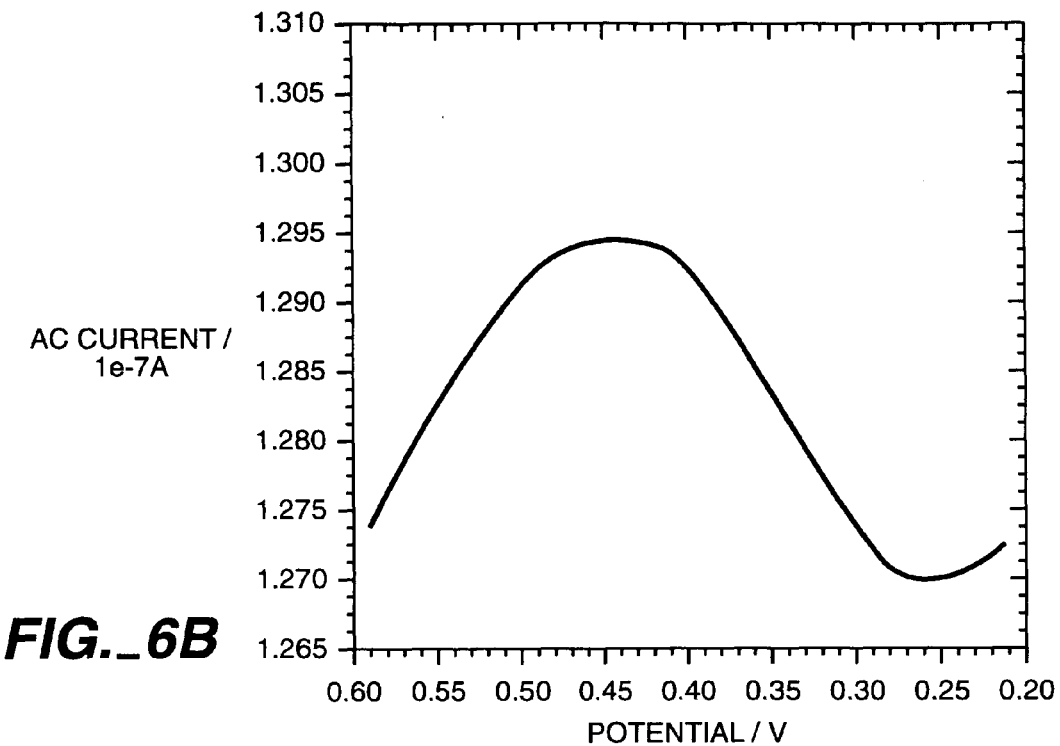
FIG._6B
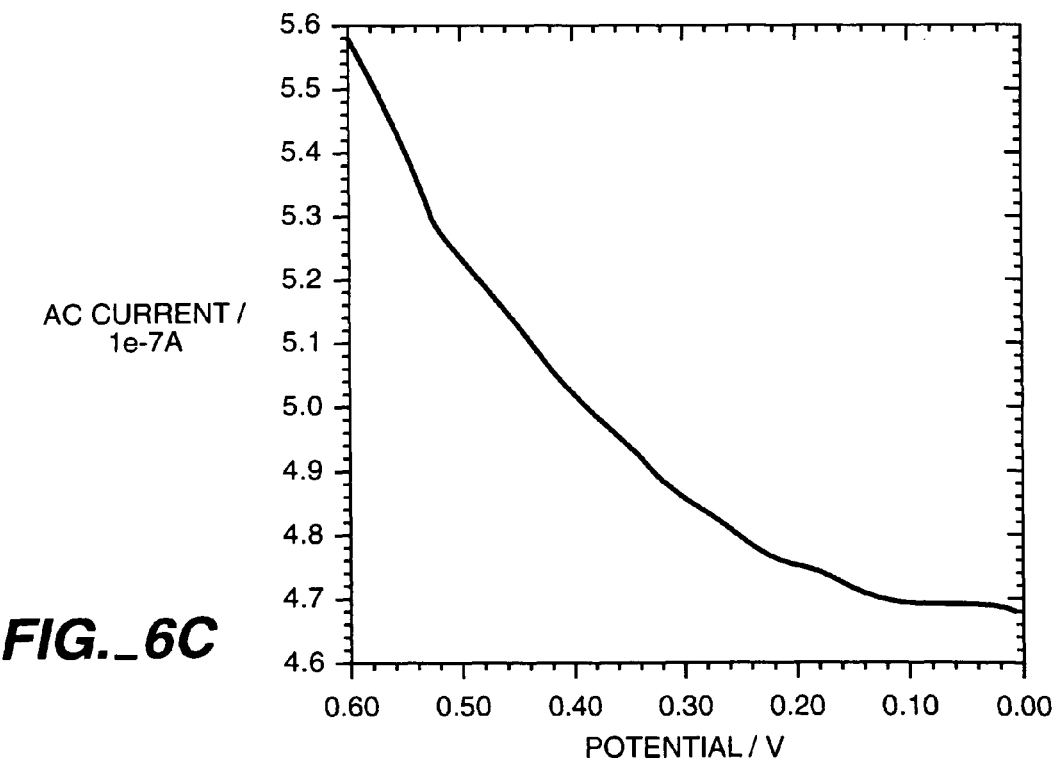
FIG._6C

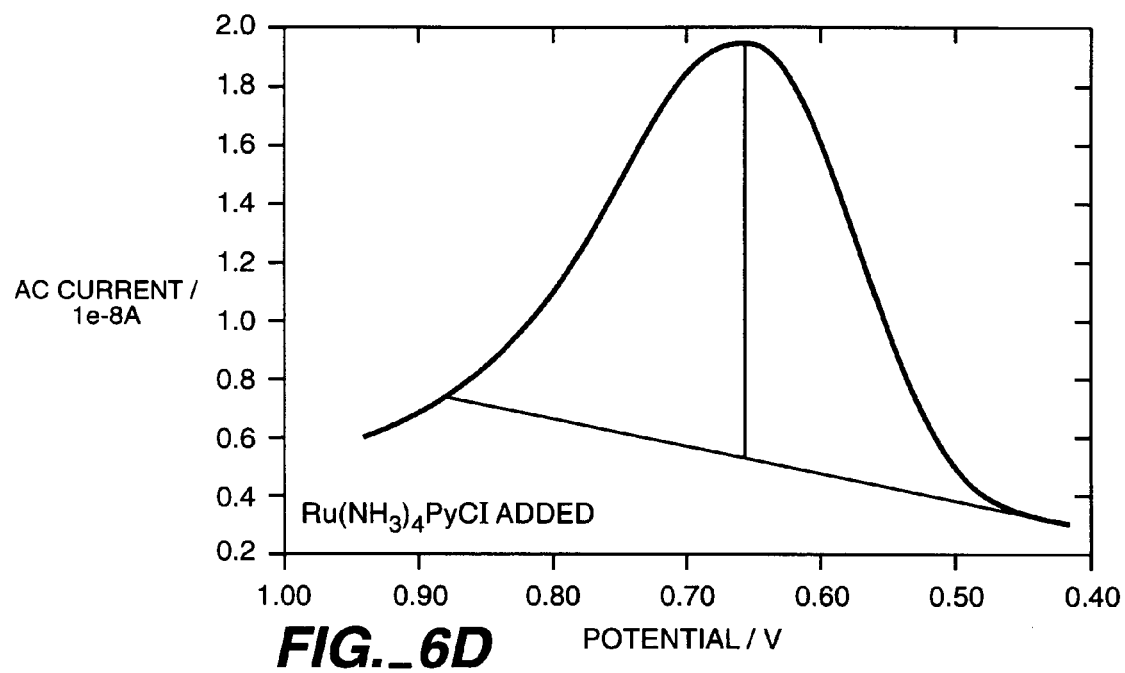
FIG._6D
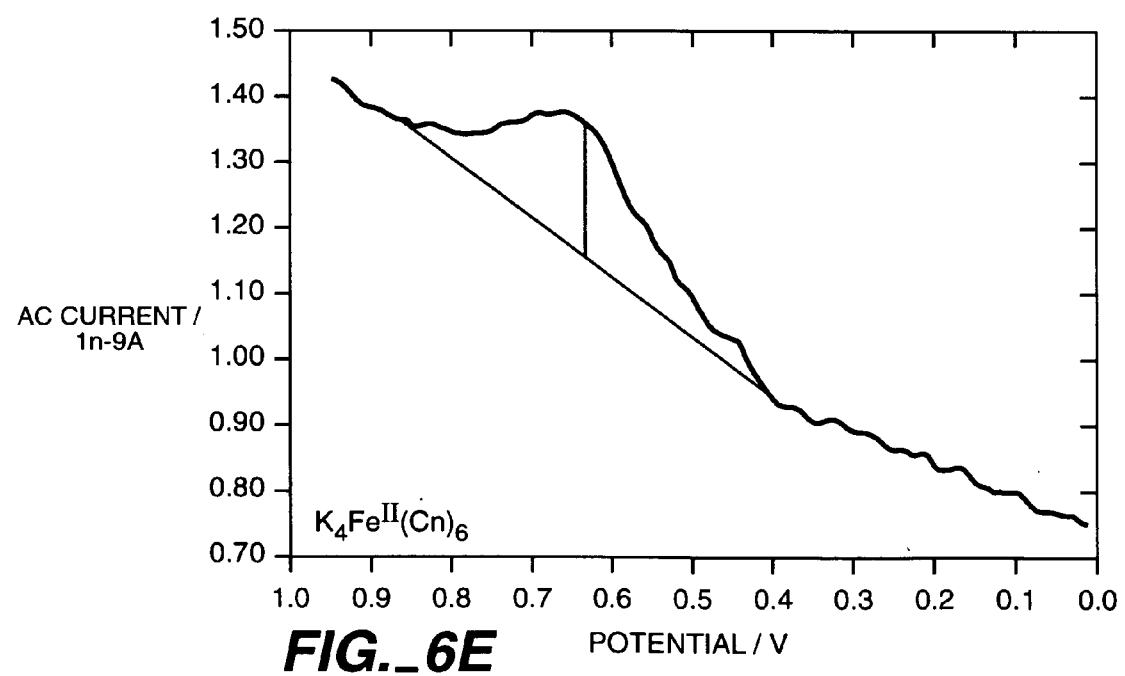
FIG._6E

ELECTRONIC METHODS FOR THE DETECTION OF ANALYTES

CROSS-REFERENCED TO RELATED APPLICATIONS

This is a continuation of U.S. patent application Ser. No. 09/096,593, filed Jun. 12, 1998, issued as U.S. Pat. No. 7,560, 237, which claims benefit of U.S. Patent Application Ser. No. 60/049,489. filed Jun. 12, 1997.

FIELD OF THE INVENTION

The invention relates to analytical methods and apparatus, and particularly to the detection of analytes, including biomolecules, using electronic techniques, particularly AC techniques.

BACKGROUND OF THE INVENTION

There are a number of assays and sensors for the detection of the presence and/or concentration of specific substances in fluids and gases. Many of these rely on specific ligand/antiligand reactions as the mechanism of detection. That is, pairs of substances (i.e. the binding pairs or ligand/antiligands) are known to bind to each other, while binding little or not at all to other substances. This has been the focus of a number of techniques that utilize these binding pairs for the detection of the complexes. These generally are done by labeling one component of the complex in some way, so as to make the entire complex detectable, using, for example, radioisotopes, fluorescent and other optically active molecules, enzymes, etc.

Other assays rely on electronic signals for detection. Of particular interest are biosensors. At least two types of biosensors are known; enzyme-based or metabolic biosensors and binding or bioaffinity sensors. See for example U.S. Pat. Nos. 4,713,347; 5,192,507; 4,920,047; 3,873,267; and references disclosed therein. While some of these known sensors use alternating current (AC) techniques, these techniques are generally limited to the detection of differences in bulk (or dielectric) impedance, and rely on the use of mediators in solution to shuttle the charge to the electrode.

Recently, there have been several preliminary reports on the use of very short connections between a binding ligand and the electrode, for direct detection, i.e. without the use of mediators. See Lötzbeyer et al., Bioelectrochemistry and Bioenergetics 42:1-6 (1997); Dong et al., Bioelectrochemistry and Bioenergetics 42:7-13 (1997).

In addition, there are a number of reports of self-assembled monolayers of conjugated oligomers on surfaces such as gold. See for example Cygan et al., J. Am. Chem. Soc. 120: 2721 (1998).

In addition, Charych et al. report on the direct colormetric detection of a receptor-ligand interaction using a bilayer assembly (Science 261:585 (1993).

Accordingly, it is an object of the invention to provide novel methods and compositions for the detection of target analytes using AC techniques.

SUMMARY OF THE INVENTION

Accordingly, in accordance with the above objects, the present invention provides methods of detecting a target analyte in a test sample comprising a redox active molecule and an analyte. The method comprises applying an input signal to the test sample and detecting a change in the faradaic impedance of the system as a result of the association of the redox active molecule with the analyte.

In an additional aspect, the invention provides methods binding the target analyte to a redox active complex comprising a redox active molecule and a binding ligand which will bind the target analyte, followed by detection of a change in the faradaic impedance of the system as a result of the association of the redox active molecule with the target analyte, if present.

The methods further comprising applying a first input signal to said redox active complex; the input signal can comprise an AC component and/or a DC component.

In a further aspect, the invention provides apparatus for the detection of analyte in a test sample, comprising a test chamber comprising at least a first and a second measuring electrode, wherein the first measuring electrode comprises a covalently attached ligand for an analyte, and an AC/DC voltage source electrically connected to the test chamber.

In an additional aspect, the present invention provides metal ion sensors comprising electrodes comprising self-assembled monolayers and at least one metal ion ligand or chelate covalently attached to the electrode via a conductive oligomer.

BRIEF DESCRIPTION OF THE DRAWINGS

FIG. 1 depicts the synthetic scheme for a conductive polymer containing an aromatic group with a substitution group. The conductive oligomer is a phenyl-acetylene Structure 5 oligomer with a single methyl R group on each phenyl ring, although other oligomers may be used, and terminates in an ethyl pyridine protecting group, as described herein, for attachment to gold electrodes.

FIG. 2 depicts the synthetic scheme for making a redox active complex comprising a RAM, in this case ferrocene, to a protein binding ligand, in this case an antibody, using a standard coupling reaction. As will be appreciated by those in the art, any proteins that either contain suitable amines or can be derivatized to contain a suitable amine can be added in this manner. Alternatively, the amine may be added to the RAM and the BL contains the carboxylic acid. Similarly, while this figure depicts the attachment of a RAM (ferrocene), a similar reaction may be done with a conductive oligomer terminating in a carboxylic acid (or an amine), for attachment to a proteinaceous binding ligand. In addition, while not depicted, "Z" linkers, as described below, may be added in between the components.

FIG. 3 depicts the synthetic scheme of a System 3 type sensor, comprising a conductive oligomer containing a redox active complex of a RAM (in this case ferrocene), with a binding ligand (in this case a biotin derivative). Any number of other RAMs and BLs may be used. Additional "Z" linkers, as described below, may be added in between the components. As for FIG. 2, a standard coupling agent (carbodimide) is used, which allows the attachment of virtually any amine- or carboxylic acid-containing moieties. The first subunit of the conductive oligomer is used, and then subsequent subunits are added.

FIG. 4 depicts a sensor of the invention, directed to the detection of antibodies to a drug. Upon the introduction of a patient sample, with binding of the antibody to its antigen, the environment of the RAM is altered, leading to a detectable change in the signal (i.e. an alteration in the faradaic impedance). The redox potential of the RAM may be altered, or there may be a signal increase or alteration. As will be appreciated by those in the art, the drug in this case could be replaced by virtually any binding ligand. In addition, this type of reaction may be run as a standard competitive type assay.

FIG. 5 depicts some possible ion sensors. The binding of ions such as Li+, Mg+2 or Na+ can alter the redox potential of the ferrocene by altering the electron withdrawing properties of the crown ethers, thus effecting a change in the signal upon binding.

FIGS. 6A, 6B, 6C, 6D and 6E depict a metal ion sensor embodiment of the invention. FIG. 6A depicts a chelate metal ion binding ligand, in this case phenanthroline, that was subsequently attached to a gold electrode, with a monolayer present. FIGS. 6B and 6C depict AC scans in the absence (6B) and presence (6C) of $FeCl_2$, showing a peak around 450 mV, the redox potential of the iron. FIG. 6D depicts the same composition in the presence of $Ru(NH_3)_4PyCl$, with a peak at around 650 mV. FIG. 6E depicts the same composition in the presence of $K_4Fe^{11}(CN)_6$, also with a peak around 650 mV.

DETAILED DESCRIPTION OF THE INVENTION

The present invention is directed to the detection of analytes using alternating current (AC) (also sometimes referred to as alternating voltage (AV)) techniques. The invention is based on the fact that at least one redox property of a redox active molecule may be altered as a result of its association with a target analyte. Without being bound by theory, it appears that changes in the environment of the redox active molecule can result in altered redox properties. That is, upon association of the analyte and the redox active molecule in some way, a measurable redox property of the redox active molecule changes, thus allowing the detection of the analyte. In particular, it has been discovered that relatively small changes in measurable redox properties can be detected using AC techniques, enabling a variety of possible biosensors.

The change in a redox property of the redox active molecule is a result of the association with an analyte. This may be due to a binding event, which may alter the conformation or accessibility of the redox active molecule, and/or a change in the local environment of the redox active molecule (for example in the solvent reorganization energy), both of which will alter the faradaic impedance of the system, which in turn results in a characteristic output signal, i.e. a different output signal than is received in the absence of the target analyte.

Accordingly, the present invention is directed to the detection of analytes using changes in the faradaic impedance of the system as a result of the binding or association of an analyte. By "faradaic impedance" herein is meant the impedance between the redox active molecule and the electrode. Changes in capacitance (e.g. due to binding of compounds to the surface or bulk dielectric capacitance) are not included in the definition of changes in faradaic impedance. This is quite different from the bulk or dielectric impedance, which is the impedance of the bulk solution between the electrodes. Many factors may change the faradaic impedance which may not effect the bulk impedance, and vice versa. As described herein, any number of perturbations of the system can result in an altered faradaic impedance, which may then serve as the basis of an assay. These include, but are not limited to, changes in electronic coupling of the redox active molecule and the electrode (often referred to as $H_{AB}$ in the literature); changes in $\lambda$, the nuclear reorganization energy, which is usually dominated by the solvent reorganization energy; changes in $E_0$ of the redox active molecule; the charge transfer impedance of the redox active molecule in the system; the mass transfer impedance of the redox active molecule in the system; changes in the redox active molecule, including exchange of ligands or metal ions; etc.

Systems relying on changes in faradaic impedance can be distinguished from prior art systems on the basis of the use of mediators. That is, prior art systems usually rely on the use of soluble mediators to shuttle electrons between the redox active molecules and the electrode; however, the present invention relies on direct electron transfer between the redox active molecule and the electrode, generally through the use of conductive oligomers. Thus, the methods of the present invention are generally run in the absence of soluble mediators that serve to electronically mediate the redox active molecule and the electrode. That is, the redox active molecules (RAMs) are directly attached to the electrodes of the invention, rather than relying on bulk diffusion mechanisms. Mediators in this context are to be distinguished by co-reductants and co-oxidants, as generally described below.

Generally, compositions and methods described in PCT US97/20014, hereby explicitly incorporated herein by reference in its entirety, find use in the present invention.

Thus the present invention is directed to methods and compositions for the detection of target analytes in test samples. By "target analyte" or "analyte" or grammatical equivalents herein is meant any molecule, compound or particle to be detected. As outlined below, target analytes preferably bind to binding ligands, as is more fully described below. As will be appreciated by those in the art, a large number of analytes may be detected using the present methods; basically, any target analyte for which a binding ligand, described below, may be made may be detected using the methods of the invention.

Suitable analytes include organic and inorganic molecules, including biomolecules. In a preferred embodiment, the analyte may be an environmental pollutant (including pesticides, insecticides, toxins, etc.); a chemical (including solvents, polymers, organic materials, etc.); therapeutic molecules (including therapeutic and abused drugs, antibiotics, etc.); biomolecules (including hormones, cytokines, proteins, lipids, carbohydrates, cellular membrane antigens and receptors (neural, hormonal, nutrient, and cell surface receptors) or their ligands, etc); whole cells (including procaryotic (such as pathogenic bacteria) and eukaryotic cells, including mammalian tumor cells); viruses (including retroviruses, herpesviruses, adenoviruses, lentiviruses, etc.); and spores; etc. Particularly preferred analytes are environmental pollutants; nucleic acids; proteins (including enzymes, antibodies, antigens, growth factors, cytokines, etc); therapeutic and abused drugs; cells; and viruses.

In a preferred embodiment, the target analytes are not nucleic acids. Similarly, a preferred embodiment utilizes target analytes that are not glucose, and redox active complexes that do not contain glucose oxidase.

In a preferred embodiment, the target analyte is a protein. As will be appreciated by those in the art, there are a large number of possible proteinaceous target analytes that may be detected using the present invention. By "proteins" or grammatical equivalents herein is meant proteins, oligopeptides and peptides, derivatives and analogs, including proteins containing non-naturally occurring amino acids and amino acid analogs, and peptidomimetic structures. The side chains may be in either the (R) or the (S) configuration. In a preferred embodiment, the amino acids are in the (S) or L-configuration. As discussed below, when the protein is used as a binding ligand, it may be desirable to utilize protein analogs to retard degradation by sample contaminants.

Suitable protein target analytes include, but are not limited to, (1) immunoglobulins, particularly IgEs, IgGs and IgMs, and particularly therapeutically or diagnostically relevant antibodies, including but not limited to, for example, antibodies to human albumin, apolipoproteins (including apolipoprotein E), human chorionic gonadotropin, cortisol, α-fetoprotein, thyroxin, thyroid stimulating hormone (TSH), antithrombin, antibodies to pharmaceuticals (including antieptileptic drugs (phenyloin, primidone, carbariezepin, ethosuximide, valproic acid, and phenobarbitol), cardioactive drugs (digoxin, lidocaine, procainamide, and disopyramide), bronchodilators (theophylline), antibiotics (chloramphenicol, sulfonamides), antidepressants, immunosuppresants, abused drugs (amphetamine, methamphetamine, cannabinoids, cocaine and opiates) and antibodies to any number of viruses (including orthomyxoviruses, (e.g. influenza virus), paramyxoviruses (e.g respiratory syncytial virus, mumps virus, measles virus), adenoviruses, rhinoviruses, coronaviruses, reoviruses, togaviruses (e.g. rubella virus), parvoviruses, poxviruses (e.g. variola virus, vaccinia virus), enteroviruses (e.g. poliovirus, coxsackievirus), hepatitis viruses (including A, B and C), herpesviruses (e.g. Herpes simplex virus, varicella-zoster virus, cytomegalovirus, Epstein-Barr virus), rotaviruses, Norwalk viruses, hantavirus, arenavirus, rhabdovirus (e.g. rabies virus), retroviruses (including HIV, HTLV-I and -II), papovaviruses (e.g. papillomavirus), polyomaviruses, and picornaviruses, and the like), and bacteria (including a wide variety of pathogenic and non-pathogenic prokaryotes of interest including *Bacillus; Vibrio*, e.g. *V. cholerae, Escherichia*, e.g. Enterotoxigenic *E. coli, Shigella*, e.g. *S. dysenteriae, Salmonella*, e.g. *S. typhi; Mycobacterium* e.g. *M. tuberculosis, M. leprae; Clostridium*, e.g. *C. botulinum, C. tetani, C. difficile, C. perfringens; Cornyebacterium*, e.g. *C. diphtheriae; Streptococcus, S. pyogenes, S. pneumoniae, Staphylococcus*, e.g. *S. aureus; Haemophilus*, e.g. *H. influenzae; Neisseria*, e.g. *N. meningitidis, N. gonorrhoeae; Yersinia*, e.g. *G. lamblia Y. pestis, Pseudomonas*, e.g. *P. aeruginosa, P. putida; Chlamydia*, e.g. *C. trachomatis; Bordetella*, e.g. *B. pertussis, Treponema*, e.g. *T. palladium*; and the like); (2) enzymes (and other proteins), including but not limited to, enzymes used as indicators of or treatment for heart disease, including creatine kinase, lactate dehydrogenase, aspartate amino transferase, troponin T, myoglobin, fibrinogen, cholesterol, triglycerides, thrombin, tissue plasminogen activator (tPA); pancreatic disease indicators including amylase, lipase, chymotrypsin and trypsin; liver function enzymes and proteins including cholinesterase, bilirubin, and alkaline phosphotase; aldolase, prostatic acid phosphatase, terminal deoxynucleotidyl transferase, and bacterial and viral enzymes such as HIV protease; (3) hormones and cytokines (many of which serve as ligands for cellular receptors) such as erythropoietin (EPO), thrombopoietin (TPO), the interleukins (including IL-1 through IL-17), insulin, insulin-like growth factors (including IGF-1 and -2), epidermal growth factor (EGF), transforming growth factors (including TGF-α and TGF-β), human growth hormone, transferrin, epidermal growth factor (EGF), low density lipoprotein, high density lipoprotein, leptin, VEGF, PDGF, ciliary neurotrophic factor, prolactin, adrenocorticotropic hormone (ACTH), calcitonin, human chorionic gonadotropin, cortisol, estradiol, follicle stimulating hormone (FSH), thyroid-stimulating hormone (TSH), leutinzing hormone (LH), progeterone, testosterone; and (4) other proteins (including α-fetoprotein, carcinoembryonic antigen CEA.

In addition, any of the biomolecules for which antibodies may be detected may be detected directly as well; that is, detection of virus or bacterial cells, therapeutic and abused drugs, etc., may be done directly.

Suitable target analytes include carbohydrates, including but not limited to, markers for breast cancer (CA15-3, CA 549, CA 27.29), mucin-like carcinoma associated antigen (MCA), ovarian cancer (CA125), pancreatic cancer (DE-PAN-2), and colorectal and pancreatic cancer (CA 19, CA 50, CA242).

Suitable target analytes include metal ions, particularly heavy and/or toxic metals, including but not limited to, aluminum, arsenic, cadmium, selenium, cobalt, copper, chromium, lead, silver and nickel.

In a preferred embodiment, the target analyte is added to or introduced to a redox active molecule or redox active complex. By "redox active molecule" or "RAM" or "electron transfer moiety" or "ETM" herein is meant a compound which is capable of reversibly, semi-reversibly, or irreversibly transferring one or more electrons. The terms "electron donor moiety", "electron acceptor moiety", and "electron transfer moieties" or grammatical equivalents herein refers to molecules capable of electron transfer under certain conditions. It is to be understood that electron donor and acceptor capabilities are relative; that is, a molecule which can lose an electron under certain experimental conditions will be able to accept an electron under different experimental conditions. It is to be understood that the number of possible electron donor moieties and electron acceptor moieties is very large, and that one skilled in the art of electron transfer compounds will be able to utilize a number of compounds in the present invention. Preferred electron transfer moieties include, but are not limited to, transition metal complexes, organic electron transfer moieties, and electrodes.

In a preferred embodiment, the electron transfer moieties are transition metal complexes. Transition metals include those whose atoms have a partial or complete d shell of electrons; elements having the atomic numbers 21-30, 39-48, 57-80 and the lanthanide series. Suitable transition metals for use in the invention include, but are not limited to, cadmium (Cd), copper (Cu), cobalt (Co), palladium (Pd), zinc (Zn), iron (Fe), ruthenium (Ru), rhodium (Rh), osmium (Os), rhenium (Re), platinium (Pt), scandium (Sc), titanium (Ti), Vanadium (V), chromium (Cr), manganese (Mn), nickel (Ni), Molybdenum (Mo), technetium (Tc), tungsten (W), and iridium (Ir). That is, the first series of transition metals, the platinum metals (Ru, Rh, Pd, Os, Ir and Pt), along with Fe, Re, W, Mo and Tc, are preferred. Particularly preferred are ruthenium, rhenium, osmium, platinium, cobalt and iron.

The transition metals are complexed with a variety of ligands, generally depicted herein as "L", to form suitable transition metal complexes, as is well known in the art. Suitable ligands fall into two categories: ligands which use nitrogen, oxygen, sulfur, carbon or phosphorus atoms (depending on the metal ion) as the coordination atoms (generally referred to in the literature as sigma (σ) donors) and organometallic ligands such as metallocene ligands (generally referred to in the literature as pi (π) donors, and depicted herein as $L_m$). Suitable nitrogen donating ligands are well known in the art and include, but are not limited to, $NIH_2$; NHR; NRR'; pyridine; pyrazine; isonicotinamide; imidazole; bipyridine and substituted derivatives of bipyridine; terpyridine and substituted derivatives; phenanthrolines, particularly 1,10-phenanthroline (abbreviated phen) and substituted derivatives of phenanthrolines such as 4,7-dimethylphenanthroline and dipyridol[3,2-a:2',3'-c]phenazine (abbreviated dppz); dipyridophenazine; 1,4,5,8,9,12-hexaazatriphenylene (abbreviated hat); 9,10-phenanthrenequinone diimine (abbreviated phi); 1,4,5,8-tetraazaphenanthrene (abbreviated tap); 1,4,8,11-tetra-azacyclotetradecane (abbreviated cyclam) and isocyanide. Substituted derivatives, including fused derivatives, may also be used. In some embodiments, porphyrins and substituted derivatives of the porphyrin family may be used. See for example, Comprehensive Coordination Chemistry, Ed. Wilkinson et al., Pergammon Press, 1987, Chapters 13.2 (pp 73-98), 21.1 (pp. 813-898) and 21.3 (pp 915-957), all of which are hereby expressly incorporated by reference.

Suitable sigma donating ligands using carbon, oxygen, sulfur and phosphorus are known in the art. For example, suitable sigma carbon donors are found in Cotton and Wilkenson, Advanced Organic Chemistry, 5th Edition, John Wiley & Sons, 1988, hereby incorporated by reference; see page 38, for example. Similarly, suitable oxygen ligands include crown ethers, water and others known in the art. Phosphines and substituted phosphines are also suitable; see page 38 of Cotton and Wilkenson.

The oxygen, sulfur, phosphorus and nitrogen-donating ligands are attached in such a manner as to allow the heteroatoms to serve as coordination atoms.

In a preferred embodiment, organometallic ligands are used. In addition to purely organic compounds for use as redox moieties, and various transition metal coordination complexes with δ-bondedorganic ligand with donor atoms as heterocyclic or exocyclic substituents, there is available a wide variety of transition metal organometallic compounds with π-bonded organic ligands (see Advanced Inorganic Chemistry, 5th Ed., Cotton & Wilkinson, John Wiley & Sons, 1988, chapter 26; Organometallics, A Concise Introduction, Elschenbroich et al., 2nd Ed., 1992, VCH; and Comprehensive Organometallic Chemistry II, A Review of the Literature 1982-1994, Abel et al. Ed., Vol. 7, chapters 7, 8, 10 & 11, Pergamon Press, hereby expressly incorporated by reference). Such organometallic ligands include cyclic aromatic compounds such as the cyclopentadienide ion $[C_5H_5(-1)]$ and various ring substituted and ring fused derivatives, such as the indenylide (−1) ion, that yield a class of bis(cyclopentadieyl)metal compounds, (i.e. the metallocenes); see for example Robins et al., J. Am. Chem. Soc. 104:1882-1893 (1982); and Gassman et al., J. Am. Chem. Soc. 108:4228-4229 (1986), incorporated by reference. Of these, ferrocene $[(C_5H_5)_2Fe]$ and its derivatives are prototypical examples which have been used in a wide variety of chemical (Connelly et al., Chem. Rev. 96:877-910 (1996), incorporated by reference) and electrochemical (Geiger et al., Advances in Organometallic Chemistry 23:1-93; and Geiger et al., Advances in Organometallic Chemistry 24:87, incorporated by reference) electron transfer or "redox" reactions. Metallocene derivatives of a variety of the first, second and third row transition metals are potential candidates as redox moieties. Other potentially suitable organometallic ligands include cyclic arenes such as benzene, to yield bis(arene)metal compounds and their ring substituted and ring fused derivatives, of which bis(benzene)chromium is a prototypical example, Other acyclic π-bonded ligands such as the allyl(−1) ion, or butadiene yield potentially suitable organometallic compounds, and all such ligands, in conjuction with other π-bonded and δ-bonded ligands constitute the general class of organometallic compounds in which there is a metal to carbon bond. Electrochemical studies of various dimers and oligomers of such compounds with bridging organic ligands, and additional non-bridging ligands, as well as with and without metal-metal bonds are potential candidate redox moieties.

As described herein, any combination of ligands may be used. Preferred combinations include: a) all ligands are nitrogen donating ligands; b) all ligands are organometallic ligands; and c) the ligand at the terminus of the conductive oligomer is a metallocene ligand and the ligand provided by the binding ligand is a nitrogen donating ligand, with the other ligands, if needed, are either nitrogen donating ligands or metallocene ligands, or a mixture.

In addition, it may be desirable to use coordination sites of the transition metal ion for attachment of the redox active molecule to either a binding ligand (directly or indirectly using a linker), to form a redox active complex, or to the electrode (frequently using a spacer such as a conductive oligomer, as is more fully described below), or both. Thus for example, when the redox active molecule is directly joined to a binding ligand, one, two or more of the coordination sites of the metal ion may be occupied by coordination atoms supplied by the binding ligand (or by the linker, if indirectly joined). In addition, or alternatively, one or more of the coordination sites of the metal ion may be occupied by a spacer used to attach the redox active molecule to the electrode.

In addition to transition metal complexes, other organic electron donors and acceptors may be used in the invention. These organic molecules include, but are not limited to, riboflavin, xanthene dyes, azine dyes, acridine orange, N,N'-dimethyl-2,7-diazapyrenium dichloride ($DAP^{2+}$), methylviologen, ethidium bromide, quinones such as N,N'-dimethylanthra(2,1,9-def:6,5,10-d'e'f')diisoquinoline dichloride ($ADIQ^{2+}$); porphyrins ([meso-tetrakis(N-methyl-x-pyridinium)porphyrin tetrachloride], varlamine blue B hydrochloride, Bindschedler's green; 2,6-dichloroindophenol, 2,6-dibromophenolindophenol; Brilliant crest blue (3-amino-9-dimethyl-amino-10-methylphenoxyazine chloride), methylene blue; Nile blue A (aminoaphthodiethylaminophenoxazine sulfate), indigo-5,5',7,7'-tetrasulfonic acid, indigo-5,5',7-trisulfonic acid; phenosafranine, indigo-5-monosulfonic acid; safranine T; bis(dimethylglyoximato)-iron(II) chloride; induline scarlet, neutral red, anthracene, coronene, pyrene, 9-phenylanthracene, rubrene, binaphthyl, DPA, phenothiazene, fluoranthene, phenanthrene, chrysene, 1,8-diphenyl-1,3,5,7-octatetracene, naphthalene, acenaphthalene, perylene, TMPD and analogs and subsitituted derivatives of these compounds.

In one embodiment, the electron donors and acceptors are redox proteins as are known in the art. However, redox proteins in many embodiments are not preferred.

The choice of the specific electron transfer moieties will be influenced by the type of electron transfer detection used, as is generally outlined below.

In some embodiments, as is outlined below, the redox active molecule is actually the analyte to be detected; for example, when redox active proteins such as metalloenzymes, cytochrome c, etc. are to be detected, they may serve as the redox active molecule. Alternatively, some metal analytes, particularly heavy metals, can also serve as the redox active molecule, in general with chelating ligands as is described herein; see for example FIG. 6.

Generally, the target analyte binds to a redox active complex. By "redox active complex" herein is meant a complex comprising at least one redox active molecule and at least one binding ligand, which, as more fully described below, may be associated in a number of different ways. In some cases, the binding ligand may also be a redox active molecule. By "binding ligand" or grammatical equivalents herein is meant a compound that is used to probe for the presence of the target analyte, and that will bind to the analyte.

As will be appreciated by those in the art, the composition of the binding ligand will depend on the composition of the target analyte. Binding ligands for a wide variety of analytes are known or can be readily found using known techniques. For example, when the analyte is a protein, the binding ligands include proteins (particularly including antibodies or fragments thereof (FAbs, etc.)) or small molecules. When the analyte is a metal ion, the binding ligand generally comprises traditional metal ion ligands or chelators, which together form the redox active molecule. Preferred binding ligand proteins include peptides. For example, when the analyte is an enzyme, suitable binding ligands include substrates and inhibitors. Antigen-antibody pairs, receptor-ligands, and carbohydrates and their binding partners are also suitable analyte-binding ligand pairs. The binding ligand may be nucleic acid, when nucleic acid binding proteins are the targets; alternatively, as is generally described in U.S. Pat. Nos. 5,270,163, 5,475,096, 5,567,588, 5,595,877, 5,637,459, 5,683,867, 5,705,337, and related patents, hereby incorporated by reference, nucleic acid "aptomers" can be developed for binding to virtually any target analyte. Similarly, there is a wide body of literature relating to the development of binding partners based on combinatorial chemistry methods. In this embodiment, when the binding ligand is a nucleic acid, preferred compositions and techniques are outlined in PCT US97/20014, hereby incorporated by reference.

By "nucleic acid" or "oligonucleotide" or grammatical equivalents herein means at least two nucleotides covalently linked together. A nucleic acid of the present invention will generally contain phosphodiester bonds, although in some cases, as outlined below, nucleic acid analogs are included that may have alternate backbones, comprising, for example, phosphoramide (Beaucage et al., Tetrahedron 49(10):1925 (1993) and references therein; Letsinger, J. Org. Chem. 35:3800 (1970); Sprinzl et al., Eur. J. Biochem. 81:579 (1977); Letsinger et al., Nucl. Acids Res. 14:3487 (1986); Sawai et al, Chem. Lett. 805 (1984), Letsinger et al., J. Am. Chem. Soc. 110:4470 (1988); and Pauwels et al., Chemica Scripta 26:141 91986)), phosphorothioate (Mag et al., Nucleic Acids Res. 19:1437 (1991); and U.S. Pat. No. 5,644,048), phosphorodithioate (Briu et al., J. Am. Chem. Soc. 111:2321 (1989), O-methylphosphoroamidite linkages (see Eckstein, Oligonucleotides and Analogues: A Practical Approach, Oxford University Press), and peptide nucleic acid backbones and linkages (see Egholm, J. Am. Chem. Soc. 114:1895 (1992); Meieret al., Chem. Int. Ed. Engl. 31:1008 (1992); Nielsen, Nature, 365:566 (1993); Carlsson et al., Nature 380:207 (1996), all of which are incorporated by reference). Other analog nucleic acids include those with positive backbones (Denpcy et al., Proc. Natl. Acad. Sci. USA 92:6097 (1995); non-ionic backbones (U.S. Pat. Nos. 5,386,023, 5,637,684, 5,602,240, 5,216,141 and 4,469,863; Kiedrowshi et al., Angew. Chem. Intl. Ed. English 30:423 (1991); Letsinger et al., J. Am. Chem. Soc. 110:4470 (1988); Letsinger et al., Nucleoside & Nucleotide 13:1597 (1994); Chapters 2 and 3, ASC Symposium Series 580, "Carbohydrate Modifications in Antisense Research", Ed. Y. S. Sanghui and P. Dan Cook; Mesmaeker et al., Bioorganic & Medicinal Chem. Lett. 4:395 (1994); Jeffs et al., J. Biomolecular NMR 34:17 (1994); Tetrahedron Lett. 37:743 (1996)) and non-ribose backbones, including those described in U.S. Pat. Nos. 5,235,033 and 5,034,506, and Chapters 6 and 7, ASC Symposium Series 580, "Carbohydrate Modifications in Antisense Research", Ed. Y. S. Sanghui and P. Dan Cook. Nucleic acids containing one or more carbocyclic sugars are also included within the definition of nucleic acids (see Jenkins et al., Chem. Soc. Rev. (1995) pp 169-176). Several nucleic acid analogs are described in Rawls, C & E News Jun. 2, 1997 page 35. All of these references are hereby expressly incorporated by reference. These modifications of the ribose-phosphate backbone may be done to facilitate the addition of RAMs or conductive oligomers, or to increase the stability and half-life of such molecules in physiological environments.

As will be appreciated by those in the art, all of these nucleic acid analogs may find use in the present invention. In addition, mixtures of naturally occurring nucleic acids and analogs can be made; for example, at the site of conductive oligomer or RAM attachment, an analog structure may be used. Alternatively, mixtures of different nucleic acid analogs, and mixtures of naturally occurring nucleic acids and analogs may be made.

In a preferred embodiment, the binding of the target analyte to the binding ligand is specific, and the binding ligand is part of a binding pair. By "specifically bind" herein is meant that the ligand binds the analyte, with specificity sufficient to differentiate between the analyte and other components or contaminants of the test sample. However, as will be appreciated by those in the art, it will be possible to detect analytes using binding which is not highly specific; for example, the systems may use different binding ligands, for example an array of different ligands, and detection of any particular analyte is via its "signature" of binding to a panel of binding ligands, similar to the manner in which "electronic noses" work. This finds particular utility in the detection of chemical analytes. The binding should be sufficient to remain bound under the conditions of the assay, including wash steps to remove non-specific binding. In some embodiments, for example in the detection of certain biomolecules, the disassociation constants of the analyte to the binding ligand will be less than about $10^{-4}$-$10^{-6}$ M$^{-1}$, with less than about $10^{-5}$ to $10^{-9}$ M$^{-1}$ being preferred and less than about $10^{-7}$-$10^{-9}$ M$^{-1}$ being particularly preferred.

Together, when present, the redox active molecule and the binding ligand comprise a redox active complex. As mentioned above, in some cases the binding ligand is the redox active molecule, and thus the redox active complex comprises the redox active binding ligand. Furthermore, in some embodiments, the target analyte is a redox active molecule, such as a metal ion or a metalloenzyme, etc.; in this case, a separate redox active molecule need not be used. In addition, there may be more than one binding ligand or redox active molecule per redox active complex, as is generally outlined below. The redox active complex may also contain additional moieties, such as cross-linking agents, labels, etc., and linkers for attachment to the electrode. The addition (generally via non-covalent binding, although as outlined herein, some interactions may be considered covalent, or post-binding covalent attachment may occur, for example through the use of cross-linking agents) of the target analyte to the redox active complex forms an assay complex. By "assay complex" herein is meant the complex of components, including target analytes, binding ligands and redox active molecules, that allows detection. The composition of the assay complex depends on the use of the different component outlined herein.

In some embodiments, as is outlined below, the redox active complex is soluble. However, in a preferred embodiment, at least one component of the assay complex is covalently attached to an electrode. In a preferred embodiment, it is generally a component of the redox active complex that is attached; that is, target analytes are not generally covalently attached to the electrode. That is, either the redox active molecule or the binding ligand is covalently attached to the electrode. By "electrode" herein is meant a conductive or semi-conductive composition, which, when connected to an electronic control and detection device, is able to transmit electrons to or from a RAM either in solution or on its surface. Thus, an electrode is an electron transfer moiety as described herein. Preferred electrodes are known in the art and include, but are not limited to, certain metals and their oxides, including gold; platinum; palladium; silicon; aluminum; metal oxide electrodes including platinum oxide, titanium oxide, tin oxide, indium tin oxide, palladium oxide, silicon oxide, aluminum oxide, molybdenum oxide ($Mo_2O_6$), tungsten oxide ($WO_3$) and ruthenium oxides; and carbon (including glassy carbon electrodes, graphite and carbon paste). Preferred electrodes include gold, silicon, carbon and metal oxide electrodes.

The electrodes described herein are depicted as a flat surface, which is only one of the possible conformations of the electrode and is for schematic purposes only. The conformation of the electrode will vary with the detection method used. For example, flat planar electrodes may be preferred for optical detection methods, or when arrays of binding ligands are made, thus requiring addressable locations for both synthesis and detection. Alternatively, for single probe analysis, the electrode may be in the form of a tube, with the conductive oligomers and binding ligands bound to the inner surface. This allows a maximum of surface area containing the target analytes to be exposed to a small volume of sample.

The systems of the invention may take on any number of configurations, as outlined below.

In a preferred embodiment, the system is used to detect pollutants, such as organic pollutants, as is depicted below in System 1:

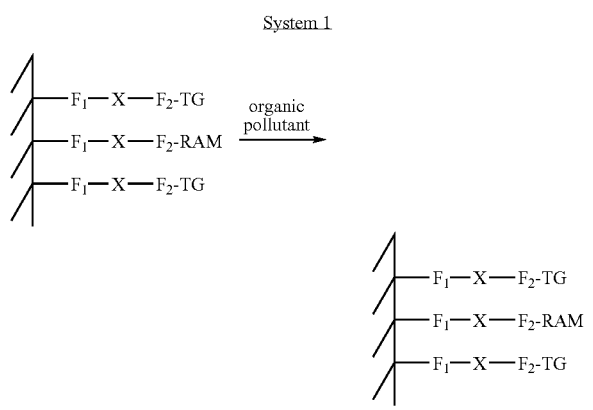

In System 1, as is described below, the hatched marks indicate an electrode, and there is preferably a monolayer on the surface. $F_1$ is a linkage that allows the covalent attachment of the electrode and the conductive oligomer or insulator, including bonds, atoms or linkers such as is described herein, for example as "A", defined below. $F_2$ is a linkage that allows the covalent attachment of the conductive oligomer or insulator, and may be a bond, an atom or a linkage as is herein described. $F_2$ may be part of the conductive oligomer, part of the insulator, part of the terminal group, part of the redox active complex or component, or exogenous to both, for example, as defined herein for "Z". X is a spacer (conductive oligomer, passivation agent or insulator, as required). RAM is a redox active molecule. TG is a terminal group, which may be chosen to influence the association of the target pollutant, such as an organic pollutant. Thus for example in this embodiment TG may be hydrophobic. The association of the pollutant on the surface will affect the local environment of the RAM, for example potentially by changing the $E_0$ of the RAM or the solvent reorganization energy, and thus results in a change in the faradaic impedance of the system in the presence of the analyte. The association in this case is not specific for a particular analyte.

Systems 2, 3, 4 and 5 depict a similar situation except that a specific interaction is exploited. Thus, the target analyte will bind to the binding ligand specifically, and is generally large as compared to the binding ligand and RAM. Upon binding, the local environment of the RAM is affected, for example potentially by changing the $E_0$ of the RAM or the solvent reorganization energy, and thus results in a change in the faradaic impedance of the system in the presence of the analyte. The target analyte in these cases could be protein, a cell, etc. In addition, any or all of these systems may be used with co-redoxants, as described below. Upon binding of the target analyte, the access of the co-redoxant to the RAM is restricted, thus resulting in either a different signal or a loss in signal, or both. In addition, as for all the systems depicted herein, the order or proximity of the individual molecules of the monolayer is not determinative.

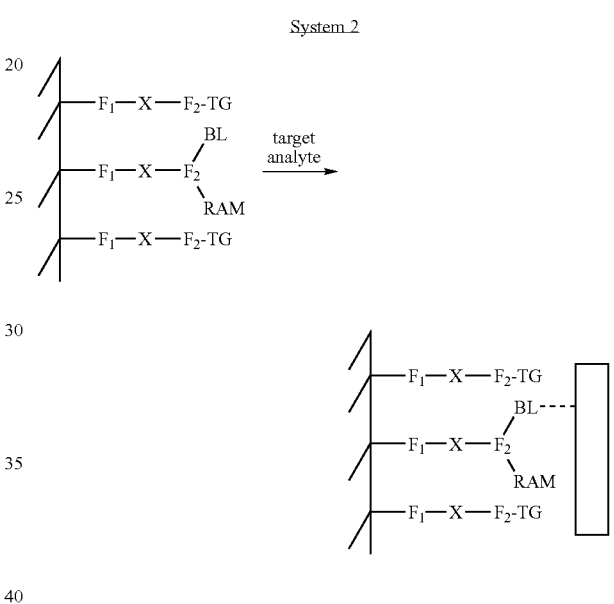

In System 2, there may be more than one RAM per binding ligand (BL); that is, the ratio of RAM to BL on the surface (depending on the relative size of the target analyte) may range from 1:1 to over 100:1. This allows an amplification of signal, in that more than one RAM is used to detect a single target analyte.

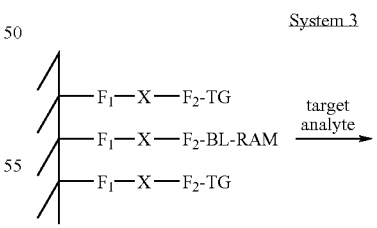

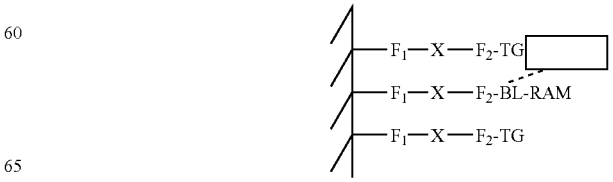

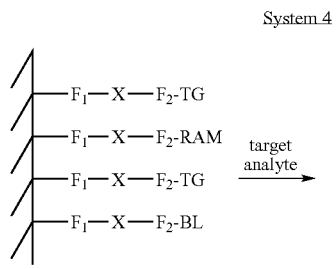

System 4

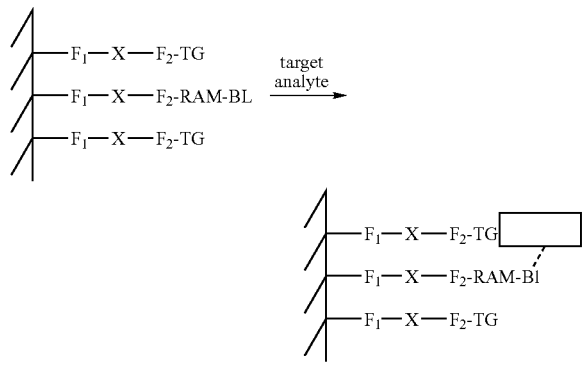

System 5

System 6 depicts a system in which binding of a target analyte theoretically affects the $H_{AB}$ between the RAM and the electrode:

System 6

System 7 depicts a similar situation, except that the binding ligand is inherent in the attachment of the RAM to the electrode; for example, it may be a peptide or nucleic acid to which the analyte binds:

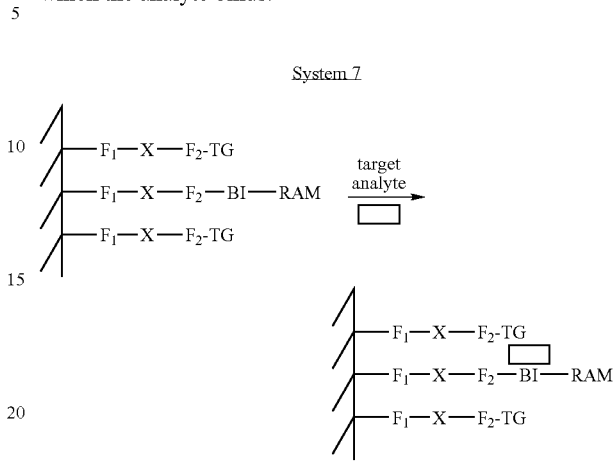

System 7

System 8 depicts a situation in which the analyte also serves as the redox active molecule; this is particularly useful in the detection of metal ions, for example heavy metal ions, which are toxic. System 8 depicts a metal ion, M, and a metal ligand, ML, although as will be appreciated by those in the art, it is quite possible to have the analyte in this case be a metalloprotein, with a BL, etc. As will be appreciated by those in the art, System 8 is particularly useful in the detection of different metal ions, using an array of different ligands; preferential binding of one metal over another would result in a panel of results that can be correlated to metal ligand binding. Moreover, different metals may have different $E_o$s and thus give different signals.

System 8

System 9 depicts a competitive-type assay which relies on a decrease in signal for detection. In this case, the target analyte is a ligand, for example carbon monoxide (CO), which are stronger ligands (SMLs, i.e. have higher binding constants) for a particular metal than the weaker metal ligand (WML) of the system.

System 9

-continued

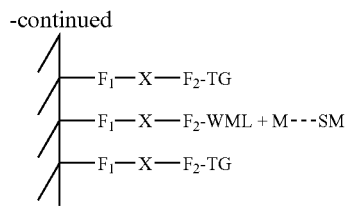

System 10 depicts a similar type of assay, which results in a change in signal rather than a decrease in signal. For example, $E_0$ and $\lambda$ could both change as a result of a new ligand binding.

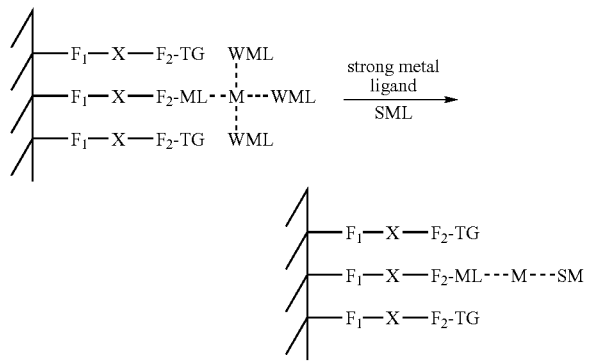

System 11 utilizes a change in the diffusion coefficient upon analyte binding for the change in faradaic impedance and mass transfer. In this embodiment, when the ligands are not covalently attached to an electrode, changes in the diffusion coefficient will alter the mass transfer impedance and thus the total faradaic impedance. That is, in some circumstances the frequency response of a redox active complex will be limited by its diffusion coefficient. Also, the charge transfer impedance may be altered by the binding of an analyte. At high frequencies, a redox active complex may not diffuse rapidly enough to reversibly transfer its electron to the electrode at a rate sufficient to generate a strong output signal. At low frequencies, the molecule has sufficient time to diffuse, and thus an output signal can be detected. In this embodiment, the use of monolayers is generally not preferred.

Thus, the result of binding to form an assay complex will generally alter the diffusion coefficient of the redox active molecule. As a result, the faradaic impedance will change. This effect will be greatest when the binding partner is large in comparison to the redox active moiety; the redox active moiety will go from being relatively small, and thus diffusing quickly, to relatively large upon binding into a complex, and diffusing much more slowly; this results in the greatest changes and is thus preferred. Similarly, binding partners of roughly equal size can also result in a detectable signal.

Alternatively, it is also possible that binding of the redox active moiety to its binding partner will cause a decrease in size. For example, some protein structures, i.e. antibodies, may have "loose" conformations that are sterically bulky, that "tighten up" as a result of binding to its partner (i.e. an antigen).

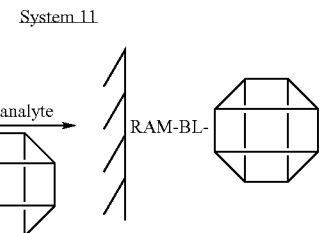

System 12 is similar to systems 10 and 11, as it is a sensor for different ligands, but it relies on a change in ligands to result in a change in $E_0$ of the system. A similar system may be used with two metals; that is, instead of adding strong metal ligands, a different metal, with different affinity for the ligands may be added, resulting in a electrochemical change.

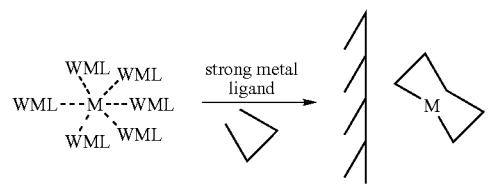

System 13 is a variation on previous systems, except that the RAM and the BL are closely associated or linked.

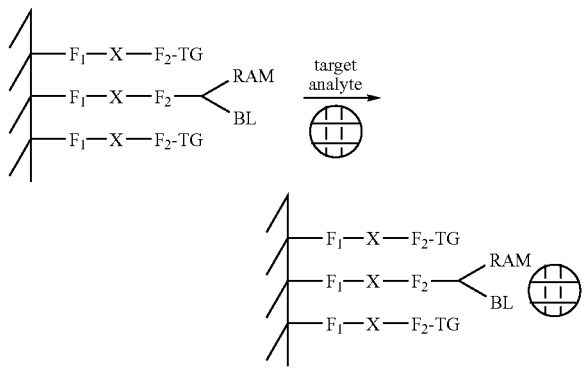

System 14 results in changes in faradaic impedance as a result of changes in $E_0$ or $H_{AB}$. In this case, the binding ligand will self-associate in some way, bringing the RAM into closer proximity to the electrode. For example, the binding ligand may be a nucleic acid (for example for the detection of a nucleic acid binding protein) or a protein (for example for the detection of proteins that inhibit or bind the binding ligand protein. Upon binding of the target, for example a protein, the conformation and thus the local environment of the RAM changes, resulting in a detectable signal. System 14 could also be run in "reverse", wherein the association of the analyte brings the RAM into proximity of the surface.

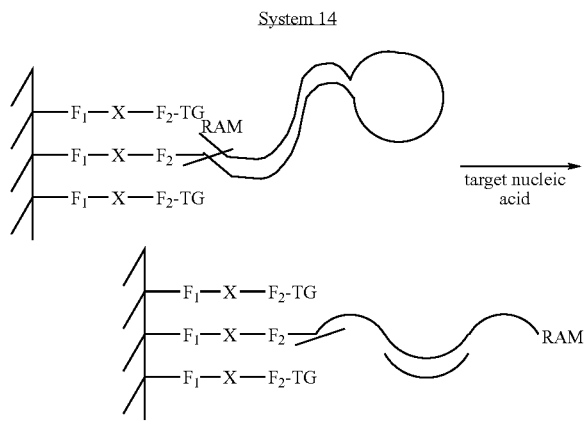

System 15 uses two binding ligands, BL1 and BL2, which may be the same or different, to alter the environment of the RAM. It may be desirable to have one of the binding ligands be a somewhat "generic" binding ligand. Changes in $E_0$ and/or impedance will result in a detectable signal.

System 18 is similar to System 9 and depicts a competitive-type assay for detecting a target analyte. In System 15, a covalently attached target analyte or target analog (TA) is competed off of the binding ligand by the addition of the target analyte, resulting in a decrease in signal.

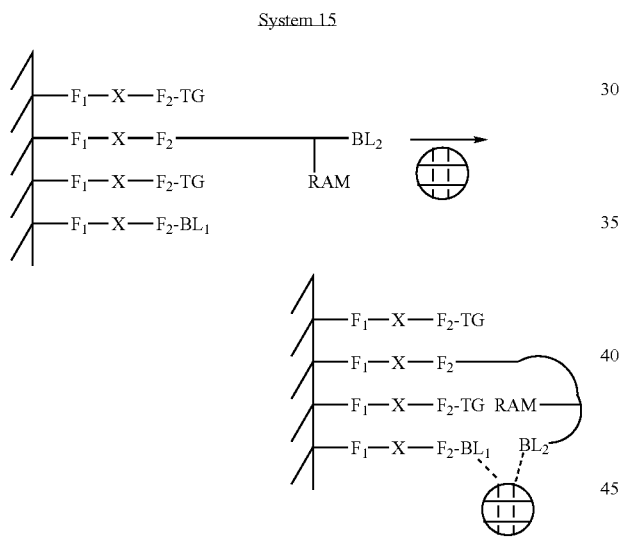

System 16 also relies on a decrease in signal. In this embodiment, a target analyte is used that will bind the metal ion-binding ligand complex in such a way as to render the metal unavailable to serve as a redox active molecule.

System 19 is a mixture of Systems 2 and 18, where the replacement of a bulky analog (TA) by a smaller target analyte (T) results in a different signal. For example, co-redoxant reactions could now occur. Alternatively, monolayers with "holes", that would allow current flow in the absence of the analog but do not in its presence, could also be used.

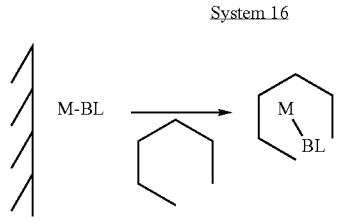

System 17 utilizes a change in metal ion affinity to a particular binding ligand to detect a change in the signal based on a different metal being present (resulting in a different $E_0$).

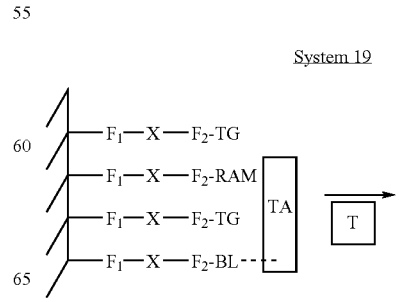

-continued

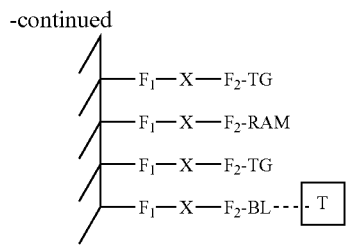

System 20 depicts a two electrode system in a competitive-type assay. This is useful in that it allows detection of an increase in signal on the second electrode, which is generally preferable to the loss of a signal.

System 20

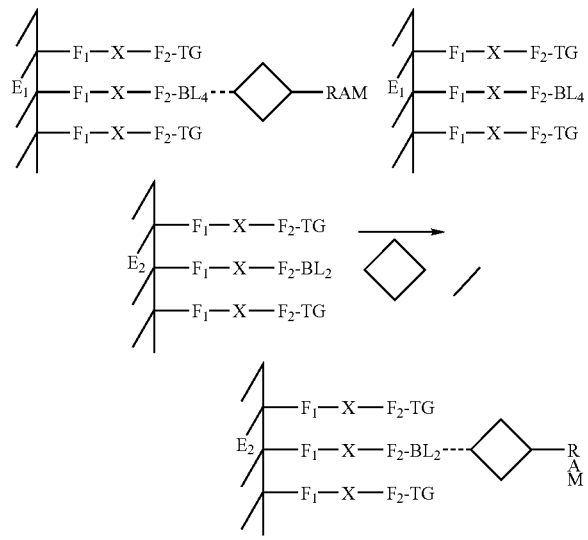

As will be appreciated by those in the art, System 20 may also be configured in several different ways. BL1 and BL2 may have different affinities for the same site on the target analyte or analog, or bind to different sites. Similarly, the other systems may also be run in two electrode systems.

In addition, it is possible to use systems like those depicted above in several other embodiments. For example, since heat will change the faradaic impedance, the systems above could be used as a heat sensor. Similarly, attachment of the RAM to the electrode using a labile or cleavable bond can allow sensing of the cleaving agent based on a decrease in signal; for example, photolabile bonds can be used to detect light (uv); substrates can be used to sense enzymes (proteases, nucleases, carbohydrases, lipases, etc.) or other cleaving agents, such as drugs that cut nucleic acids, etc.

In the systems described above, the redox active complex is covalently attached to the electrode. This may be accomplished in any number of ways, as will be apparent to those in the art. In a preferred embodiment, one or both of the redox active molecule and the binding ligand are attached, via a spacer, to the electrode, using the techniques and compositions outlined below. By "spacer" herein is meant a moiety which holds the redox active complex off the surface of the electrode. In a preferred embodiment, the spacer used to attach the redox active molecule is a conductive oligomer as outlined herein, although suitable spacer moieties include passivation agents and insulators as outlined below. The spacer moieties may be substantially non-conductive. In general, the length of the spacer is as outlined for conductive polymers and passivation agents. As will be appreciated by those in the art, if the spacer becomes too long, the electronic coupling between the redox active molecule and the electrode will decrease rapidly.

In a preferred embodiment, the redox active molecule will be attached via a conductive oligomer, such that detection of changes in faradaic impedance as between the redox active molecule and the electrode can be detected. Other components of the system may be attached using other spacers; for example, when the binding ligand and the redox active molecule are attached separately, as is generally depicted in System 2, the binding ligand may be attached via a non-conductive oligomer spacer.

In a preferred embodiment, the spacer is a conductive oligomer. By "conductive oligomer" herein is meant a substantially conducting oligomer, preferably linear, some embodiments of which are referred to in the literature as "molecular wires".

By "conductive oligomer" herein is meant a substantially conducting oligomer, preferably linear, some embodiments of which are referred to in the literature as "molecular wires". By "substantially conducting" herein is meant that the rate of electron transfer through the conductive oligomer is generally not the rate limiting step in the detection of the target analyte, although as noted below, systems which use spacers that are the rate limiting step are also acceptable. Stated differently, the resistance of the conductive oligomer is less than that of the other components of the system. Generally, the conductive oligomer has substantially overlapping π-orbitals, i.e. conjugated π-orbitals, as between the monomeric units of the conductive oligomer, although the conductive oligomer may also contain one or more sigma (σ) bonds. Additionally, a conductive oligomer may be defined functionally by its ability to pass electrons into or from an attached component. Furthermore, the conductive oligomer is more conductive than the insulators as defined herein.

In a preferred embodiment, the conductive oligomers have a conductivity, S, of from between about $10^{-6}$ to about $10^{4}$ $\Omega^{-1}$ cm$^{-1}$, with from about $10^{-5}$ to about $10^{3}$ $\Omega^{-1}$ cm$^{-1}$ being preferred, with these S values being calculated for molecules ranging from about 20 Å to about 200 Å. As described below, insulators have a conductivity S of about $10^{-7}$ $\Omega^{-1}$ cm$^{-1}$ or lower, with less than about $10^{-8}$ $\Omega^{-1}$ cm$^{-1}$ being preferred. See generally Gardner et al., Sensors and Actuators A 51 (1995) 57-66, incorporated herein by reference.

Desired characteristics of a conductive oligomer include high conductivity, sufficient solubility in organic solvents and/or water for synthesis and use of the compositions of the invention, and preferably chemical resistance to reactions that occur i) during synthesis of the systems of the invention, ii) during the attachment of the conductive oligomer to an electrode, or iii) during test assays.

The oligomers of the invention comprise at least two monomeric subunits, as described herein. As is described more fully below, oligomers include homo- and hetero-oligomers, and include polymers.

In a preferred embodiment, the conductive oligomer has the structure depicted in Structure 1:

Structure 1

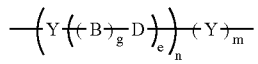

As will be understood by those in the art, all of the structures depicted herein may have additional atoms or structures; i.e. the conductive oligomer of Structure 1 may be attached to redox active molecules such as electrodes, transition metal complexes, organic electron transfer moieties, and metallocenes, and to binding ligands, or to several of these. Unless otherwise noted, the conductive oligomers depicted herein will be attached at the left side to an electrode; that is, as depicted in Structure 1, the left "Y" is connected to the electrode as described herein and the right "Y", if present, is attached to the redox active complex, either directly or through the use of a linker, as is described herein.

In this embodiment, Y is an aromatic group, n is an integer from 1 to 50, g is either 1 or zero, e is an integer from zero to 10, and m is zero or 1. When g is 1, B-D is a conjugated bond, preferably selected from acetylene, alkene, substituted alkene, amide, azo, —C=N— (including —N=C—, —CR=N— and —N=CR—), —Si=Si—, and —Si=C— (including —C=Si—, —Si=CR— and —CR=Si—). When g is zero, e is preferably 1, D is preferably carbonyl, or a heteroatom moiety, wherein the heteroatom is selected from oxygen, sulfur, nitrogen or phosphorus. Thus, suitable heteroatom moieties include, but are not limited to, —NH and —NR, wherein R is as defined herein; substituted sulfur; sulfonyl (—SO$_2$—) sulfoxide (—SO—); phosphine oxide (—PO— and —RPO—); and thiophosphine (—PS— and —RPS—). However, when the conductive oligomer is to be attached to a gold electrode, as outlined below, sulfur derivatives are not preferred.

By "aromatic group" or grammatical equivalents herein is meant an aromatic monocyclic or polycyclic hydrocarbon moiety generally containing 5 to 14 carbon atoms (although larger polycyclic rings structures may be made) and any carbocylic ketone or thioketone derivative thereof, wherein the carbon atom with the free valence is a member of an aromatic ring. Aromatic groups include arylene groups and aromatic groups with more than two atoms removed. For the purposes of this application aromatic includes heterocycle. "Heterocycle" or "heteroaryl" means an aromatic group wherein 1 to 5 of the indicated carbon atoms are replaced by a heteroatom chosen from nitrogen, oxygen, sulfur, phosphorus, boron and silicon wherein the atom with the free valence is a member of an aromatic ring, and any heterocyclic ketone and thioketone derivative thereof. Thus, heterocycle includes thienyl, furyl, pyrrolyl, pyrimidinyl, oxalyl, indolyl, purinyl, quinolyl, isoquinolyl, thiazolyl, imidozyl, etc.

Importantly, the Y aromatic groups of the conductive oligomer may be different, i.e. the conductive oligomer may be a heterooligomer. That is, a conductive oligomer may comprise a oligomer of a single type of Y groups, or of multiple types of Y groups. Thus, in a preferred embodiment, when a barrier monolayer is used as is described below, one or more types of Y groups are used in the conductive oligomer within the monolayer with a second type(s) of Y group used above the monolayer level. Thus, as is described herein, the conductive oligomer may comprise Y groups that have good packing efficiency within the monolayer at the electrode surface, and a second type(s) of Y groups with greater flexibility and hydrophilicity above the monolayer level to facilitate target analyte binding. For example, unsubstituted benzyl rings may comprise the Y rings for monolayer packing, and substituted benzyl rings may be used above the monolayer. Alternatively, heterocylic rings, either substituted or unsubstituted, may be used above the monolayer. Additionally, in one embodiment, heterooligomers are used even when the conductive oligomer does not extend out of the monolayer.

The aromatic group may be substituted with a substitution group, generally depicted herein as R. R groups may be added as necessary to affect the packing of the conductive oligomers, i.e. when the conductive oligomers form a monolayer on the electrode, R groups may be used to alter the association of the oligomers in the monolayer. R groups may also be added to 1) alter the solubility of the oligomer or of compositions containing the oligomers; 2) alter the conjugation or electrochemical potential of the system; and 3) alter the charge or characteristics at the surface of the monolayer.

In a preferred embodiment, when the conductive oligomer is greater than three subunits, R groups are preferred to increase solubility when solution synthesis is done. However, the R groups, and their positions, are chosen to minimally effect the packing of the conductive oligomers on a surface, particularly within a monolayer, as described below. In general, only small R groups are used within the monolayer, with larger R groups generally above the surface of the monolayer. Thus for example the attachment of methyl groups to the portion of the conductive oligomer within the monolayer to increase solubility is preferred, with attachment of longer alkoxy groups, for example, C3 to C10, is preferably done above the monolayer surface. In general, for the systems described herein, this generally means that attachment of sterically significant R groups is not done on any of the first three oligomer subunits, depending on the length of the insulator molecules.

Suitable R groups include, but are not limited to, hydrogen, alkyl, alcohol, aromatic, amino, amido, nitro, ethers, esters, aldehydes, sulfonyl, silicon moieties, halogens, sulfur containing moieties, phosphorus containing moieties, and ethylene glycols. In the structures depicted herein, R is hydrogen when the position is unsubstituted. It should be noted that some positions may allow two substitution groups, R and R', in which case the R and R' groups may be either the same or different.

By "alkyl group" or grammatical equivalents herein is meant a straight or branched chain alkyl group, with straight chain alkyl groups being preferred. If branched, it may be branched at one or more positions, and unless specified, at any position. The alkyl group may range from about 1 to about 30 carbon atoms (C1-C30), with a preferred embodiment utilizing from about 1 to about 20 carbon atoms (C1-C20), with about C1 through about C12 to about C15 being preferred, and C1 to C5 being particularly preferred, although in some embodiments the alkyl group may be much larger. Also included within the definition of an alkyl group are cycloalkyl groups such as C5 and C6 rings, and heterocyclic rings with nitrogen, oxygen, sulfur or phosphorus. Alkyl also includes heteroalkyl, with heteroatoms of sulfur, oxygen, nitrogen, and silicone being preferred. Alkyl includes substituted alkyl groups. By "substituted alkyl group" herein is meant an alkyl group further comprising one or more substitution moieties "R", as defined above.

By "amino groups" or grammatical equivalents herein is meant —NH$_2$, —NHR and —NR$_2$ groups, with R being as defined herein.

By "nitro group" herein is meant an —NO$_2$ group.

By "sulfur containing moieties" herein is meant compounds containing sulfur atoms, including but not limited to, thia-, thio- and sulfo-compounds, thiols (—SH and —SR), and sulfides (—RSR—). By "phosphorus containing moieties" herein is meant compounds containing phosphorus, including, but not limited to, phosphines and phosphates. By "silicon containing moieties" herein is meant compounds containing silicon.

By "ether" herein is meant an —O—R group. Preferred ethers include alkoxy groups, with —O—$(CH_2)_2CH_3$ and —O—$(CH_2)_4CH_3$ being preferred.

By "ester" herein is meant a —COOR group.

By "halogen" herein is meant bromine, iodine, chlorine, or fluorine. Preferred substituted alkyls are partially or fully halogenated alkyls such as $CF_3$, etc.

By "aldehyde" herein is meant —RCOH groups.

By "alcohol" herein is meant —OH groups, and alkyl alcohols —ROH.

By "amido" herein is meant —RCONH— or RCONR— groups.

By "ethylene glycol" herein is meant a —(O—$CH_2$—$CH_2$)$_n$— group, although each carbon atom of the ethylene group may also be singly or doubly substituted, i.e. —(O—$CR_2$—$CR_2$)$_n$—, with R as described above. Ethylene glycol derivatives with other heteroatoms in place of oxygen (i.e. —(N—$CH_2$—$CH_2$)$_n$— or —(S—$CH_2$—$CH_2$)$_n$—, or with substitution groups) are also preferred.

Preferred substitution groups include, but are not limited to, methyl, ethyl, propyl, alkoxy groups such as —O—$(CH_2)_2$$CH_3$ and —O—$(CH_2)_4CH_3$ and ethylene glycol and derivatives thereof.

Preferred aromatic groups include, but are not limited to, phenyl, naphthyl, naphthalene, anthracene, phenanthroline, pyrole, pyridine, thiophene, porphyrins, and substituted derivatives of each of these, included fused ring derivatives.

In the conductive oligomers depicted herein, when g is 1, B-D is a bond linking two atoms or chemical moieties. In a preferred embodiment, B-D is a conjugated bond, containing overlapping or conjugated π-orbitals.

Preferred B-D bonds are selected from acetylene (—C≡C—, also called alkyne or ethyne), alkene (—CH═CH—, also called ethylene), substituted alkene (—CR═CR—, —CH═CR— and —CR═CH—), amide (—NH—CO— and —NR—CO— or —CO—NH— and —CO—NR—), azo (—N═N—), esters and thioesters (—CO—O—, —O—CO—, —CS—O— and —O—CS—) and other conjugated bonds such as (—CH═N—, —CR═N—, —N═CH— and —N═CR—), (—SiH═SiH—, —SiR═SiH—, —SiR═SiH—, and —SiR═SiR—), (—SiH═CH—, —SiR═CH—, —SiH═CR—, —SiR═CR—, —CH═SiH—, —CR═SiH—, —CH═SiR—, and —CR═SiR—). Particularly preferred B-D bonds are acetylene, alkene, amide, and substituted derivatives of these three, and azo. Especially preferred B-D bonds are acetylene, alkene and amide. The oligomer components attached to double bonds may be in the trans or cis conformation, or mixtures. Thus, either B or D may include carbon, nitrogen or silicon. The substitution groups are as defined as above for R.

When g=0 in the Structure 2 conductive oligomer, e is preferably 1 and the D moiety may be carbonyl or a heteroatom moiety as defined above.

As above for the Y rings, within any single conductive oligomer, the B-D bonds (or D moieties, when g=0) may be all the same, or at least one may be different. For example, when m is zero, the terminal B-D bond may be an amide bond, and the rest of the B-D bonds may be acetylene bonds. Generally, when amide bonds are present, as few amide bonds as possible are preferable, but in some embodiments all the B-D bonds are amide bonds. Thus, as outlined above for the Y rings, one type of B-D bond may be present in the conductive oligomer within a monolayer as described below, and another type above the monolayer level, to give greater flexibility.

In the structures depicted herein, n is an integer from 1 to 50, although longer oligomers may also be used (see for example Schumm et al., Angew. Chem. Int. Ed. Engl. 1994 33(13):1360). Without being bound by theory, it appears that for efficient binding of target analytes on a surface, the binding should occur at a distance from the surface, i.e. the kinetics of binding increase as a function of the distance from the surface, particularly for larger analytes. Accordingly, the length of the conductive oligomer is such that the closest portion of the redox active complex is positioned from about 6 Å to about 100 Å (although distances of up to 500 Å may be used) from the electrode surface, with from about 25 Å to about 60 Å being preferred. In a preferred embodiment, the length of the conductive oligomer is greater than $(CH_2)_6$ linkers, with greater than $(CH_2)_{10}$ being preferred and greater than about $(CH_2)_{16}$ being particularly preferred. Accordingly, n will depend on the size of the aromatic group, but generally will be from about 1 to about 20, with from about 2 to about 15 being preferred and from about 3 to about 10 being especially preferred.

In the structures depicted herein, m is either 0 or 1. That is, when m is 0, the conductive oligomer may terminate in the B-D bond or D moiety, i.e. the D atom is attached to the component of the redox active complex either directly or via a linker. In some embodiments, there may be additional atoms, such as a linker, attached between the conductive oligomer and the component of the redox active complex to which it is attached. Additionally, as outlined below, the D atom may be a nitrogen atom of a redox active complex, for example an amine of a protein. Alternatively, when m is 1, the conductive oligomer may terminate in Y, an aromatic group, i.e. the aromatic group is attached to the redox active complex or linker.

As will be appreciated by those in the art, a large number of possible conductive oligomers may be utilized. These include conductive oligomers falling within the Structure 1 and Structure 8 formulas, as well as other conductive oligomers, as are generally known in the art, including for example, compounds comprising fused aromatic rings or Teflon®-like oligomers, such as —$(CF_2)_n$—, —$(CHF)_n$— and —$(CFR)_n$—. See for example, Schumm et al., angew. Chem. Intl. Ed. Engl. 33:1361 (1994); Grosshenny et al., Platinum Metals Rev. 40(1):26-35 (1996); Tour, Chem. Rev. 96:537-553 (1996); Hsung et al., Organometallics 14:4808-4815 (1995; and references cited therein, all of which are expressly incorporated by reference.

Particularly preferred conductive oligomers of this embodiment are depicted below:

Structure 2

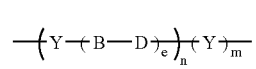

Structure 2 is Structure 1 when g is 1. Preferred embodiments of Structure 2 include: e is zero, Y is pyrole or substituted pyrole; e is zero, Y is thiophene or substituted thiophene; e is zero, Y is furan or substituted furan; e is zero, Y is phenyl or substituted phenyl; e is zero, Y is pyridine or substituted pyridine; e is 1, B-D is acetylene and Y is phenyl or substituted phenyl (see Structure 4 below). A preferred embodiment of Structure 2 is also when e is one, depicted as Structure 3 below:

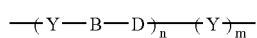

Structure 3

Preferred embodiments of Structure 3 are: Y is phenyl or substituted phenyl and B-D is azo; Y is phenyl or substituted phenyl and B-D is alkene; Y is pyridine or substituted pyridine and B-D is acetylene; Y is thiophene or substituted thiophene and B-D is acetylene; Y is furan or substituted furan and B-D is acetylene; Y is thiophene or furan (or substituted thiophene or furan) and B-D are alternating alkene and acetylene bonds.

Most of the structures depicted herein utilize a Structure 3 conductive oligomer. However, any Structure 4 oligomers may be substituted with a Structure 1, 2 or 8 oligomer, or other conducting oligomer, and the use of such Structure 3 depiction is not meant to limit the scope of the invention.

Particularly preferred embodiments of Structure 3 include Structures 4, 5, 6 and 7, depicted below:

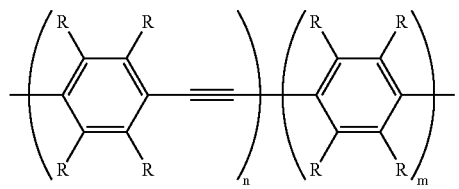

Structure 4

Particularly preferred embodiments of Structure 4 include: n is two, m is one, and R is hydrogen; n is three, m is zero, and R is hydrogen; and the use of R groups to increase solubility.

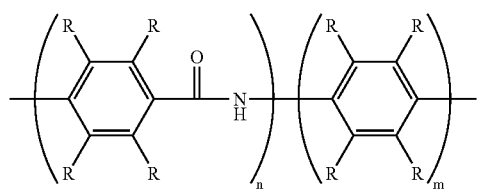

Structure 5

When the B-D bond is an amide bond, as in Structure 5, the conductive oligomers are pseudopeptide oligomers. Although the amide bond in Structure 5 is depicted with the carbonyl to the left, i.e. —CONH—, the reverse may also be used, i.e. —NHCO—. Particularly preferred embodiments of Structure 5 include: n is two, m is one, and R is hydrogen; n is three, m is zero, and R is hydrogen (in this embodiment, the terminal nitrogen (the D atom) may be the nitrogen of the amino-modified ribose); and the use of R groups to increase solubility.

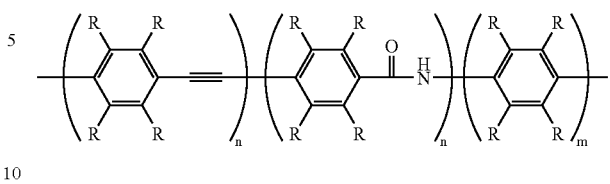

Structure 6

Preferred embodiments of Structure 6 include the first n is two, second n is one, m is zero, and all R groups are hydrogen, or the use of R groups to increase solubility.

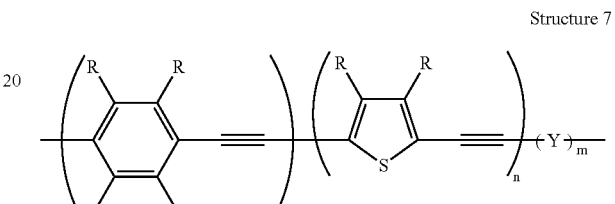

Structure 7

Preferred embodiments of Structure 7 include: the first n is three, the second n is from 1-3, with m being either 0 or 1, and the use of R groups to increase solubility.

In a preferred embodiment, the conductive oligomer has the structure depicted in Structure 8:

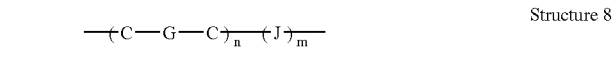

Structure 8

In this embodiment, C are carbon atoms, n is an integer from 1 to 50, m is 0 or 1, J is a heteroatom selected from the group consisting of nitrogen, silicon, phosphorus, sulfur, carbonyl or sulfoxide, and G is a bond selected from alkane, alkene or acetylene, such that together with the two carbon atoms the C-G-C group is an alkene (—CH=CH—), substituted alkene (—CR=CR—) or mixtures thereof (—CH=CR— or —CR=CH—), acetylene (—C≡C—), or alkane (—CR$_2$—CR$_2$—, with R being either hydrogen or a substitution group as described herein). The G bond of each subunit may be the same or different than the G bonds of other subunits; that is, alternating oligomers of alkene and acetylene bonds could be used, etc. However, when G is an alkane bond, the number of alkane bonds in the oligomer should be kept to a minimum, with about six or less sigma bonds per conductive oligomer being preferred. Alkene bonds are preferred, and are generally depicted herein, although alkane and acetylene bonds may be substituted in any structure or embodiment described herein as will be appreciated by those in the art.

In a preferred embodiment, the m of Structure 8 is zero. In a particularly preferred embodiment, m is zero and G is an alkene bond, as is depicted in Structure 9:

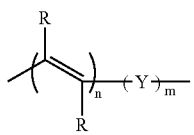

Structure 9

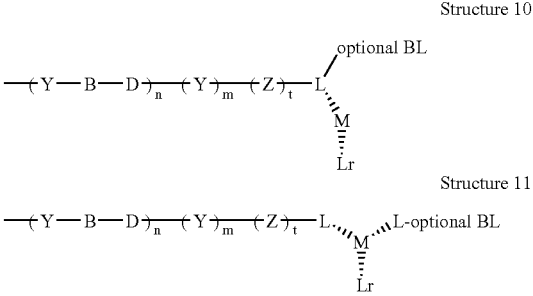

The alkene oligomer of structure 9, and others depicted herein, are generally depicted in the preferred trans configuration, although oligomers of cis or mixtures of trans and cis may also be used. As above, R groups may be added to alter the packing of the compositions on an electrode, the hydrophilicity or hydrophobicity of the oligomer, and the flexibility, i.e. the rotational, torsional or longitudinal flexibility of the oligomer. n is as defined above.

In a preferred embodiment, R is hydrogen, although R may be also alkyl groups and polyethylene glycols or derivatives.

In an alternative embodiment, the conductive oligomer may be a mixture of different types of oligomers, for example of structures 1 and 8.

The conductive oligomers are covalently attached to a component of the redox active complex, either the binding ligand, or the redox active molecule, or both, as is generally outlined in the systems described above. By "covalently attached" herein is meant that two moieties are attached by at least one bond, including sigma bonds, pi bonds and coordination bonds.

The method of attachment of the redox active complex to the spacer (also sometimes referred to herein as an attachment linker, which may be either an insulator or conductive oligomer) will generally be done as is known in the art, and will depend on both the composition of the attachment linker and the capture binding ligand. In general, the redox active complexes are attached to the attachment linker through the use of functional groups on each that can then be used for attachment. Preferred functional groups for attachment are amino groups, carboxy groups, oxo groups and thiol groups. These functional groups can then be attached, either directly or indirectly through the use of a linker, sometimes depicted herein as "Z". Linkers are well known in the art; for example, homo- or hetero-bifunctional linkers as are well known (see 1994 Pierce Chemical Company catalog, technical section on cross-linkers, pages 155-200, incorporated herein by reference). Preferred Z linkers include, but are not limited to, alkyl groups (including substituted alkyl groups and alkyl groups containing heteroatom moieties), with short alkyl groups, esters, amide, amine, epoxy groups and ethylene glycol and derivatives being preferred, with propyl, acetylene, and $C_2$ alkene being especially preferred. Z may also be a sulfone group, forming sulfonamide linkages.

A preferred attachment of redox active molecules that are transition metal complexes utilizes either a transition metal ligand (including coordination atoms) on the terminus of the conductive oligomer, that serves to attach the redox active molecule to the conductive oligomer, as is generally depicted below in Structures 10 and 11. Both Structure 10 and 11 depict a structure 3 conductive oligomer, although other oligomers may be used. Similarly, if a binding ligand is attached (for example as shown in System 4), the metal ligand can either be attached to the binding ligand (i.e. exogeneously added, for example using a Z linker) or can be contributed by the binding ligand itself (for example, using a nitrogen of an amino acid side chain).

L are the co-ligands, that provide the coordination atoms for the binding of the metal ion. As will be appreciated by those in the art, the number and nature of the co-ligands will depend on the coordination number of the metal ion. Mono-, di- or polydentate co-ligands may be used at any position. Thus, for example, when the metal has a coordination number of six, the L from the terminus of the conductive oligomer, the L contributed from the binding ligand (if present) and r, add up to six. Thus, when the metal has a coordination number of six, r may range from zero (when all coordination atoms are provided by the other ligands) to five, when all the co-ligands are monodentate. Thus generally, r will be from 0 to 8, depending on the coordination number of the metal ion and the choice of the other ligands.

In one embodiment, the metal ion has a coordination number of six and both the ligand attached to the conductive oligomer and the ligand either attached or contributed by the binding ligand are at least bidentate; that is, r is preferably zero, one (i.e. the remaining co-ligand is bidentate) or two (two monodentate co-ligands are used).

As will be appreciated in the art, the co-ligands can be the same or different.

When one or more of the co-ligands is an organometallic ligand, the ligand is generally attached via one of the carbon atoms of the organometallic ligand, although attachment may be via other atoms for heterocyclic ligands. Preferred organometallic ligands include metallocene ligands, including substituted derivatives and the metalloceneophanes (see page 1174 of Cotton and Wilkenson, supra). For example, derivatives of metallocene ligands such as methylcyclopentadienyl, with multiple methyl groups being preferred, such as pentamethylcyclopentadienyl, can be used to increase the stability of the metallocene. In a preferred embodiment, only one of the two metallocene ligands of a metallocene are derivatized.

In this way, redox active complexes may be attached, including binding ligands comprising proteins, lectins, nucleic acids, small organic molecules, carbohydrates, etc.

A preferred embodiment utilizes proteinaceous binding ligands. As is known in the art, any number of techniques may be used to attach a proteinaceous binding ligand to an attachment linker, as is outlined above for the attachment of a redox active complex to the spacer; see also FIGS. 2 and 3. A wide variety of techniques are known to add moieties to proteins. Similar techniques can be used to add the binding ligand to the redox active molecule, for example as depicted in System 3, 4 or 5, as will be appreciated by those in the art.

A preferred embodiment utilizes nucleic acids as the binding ligand, with techniques outlined in PCT US97/20014 being useful for attachment.

One end of the attachment linker is linked to the redox active complex, and the other end (although as will be appreciated by those in the art, it need not be the exact terminus for either) is attached to the electrode. Thus, any of structures depicted herein may further comprise a redox active complex or system component effectively as a terminal group.

The covalent attachment of the conductive oligomer containing the redox active molecule (and the attachment of other spacer molecules) may be accomplished in a variety of ways, depending on the electrode and the conductive oligomer used. Generally, some type of linker is used, as depicted below as "A" in Structure 12, where X is the conductive oligomer, and the hatched surface is the electrode:

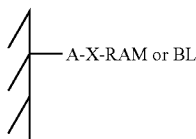

Structure 12

In this embodiment, A is a linker or atom. The choice of "A" will depend in part on the characteristics of the electrode. Thus, for example, A may be a sulfur moiety when a gold electrode is used. Alternatively, when metal oxide electrodes are used, A may be a silicon (silane) moiety attached to the oxygen of the oxide (see for example Chen et al., Langmuir 10:3332-3337 (1994); Lenhard et al., J. Electroanal. Chem. 78:195-201 (1977), both of which are expressly incorporated by reference). When carbon based electrodes are used, A may be an amino moiety (preferably a primary amine; see for example Deinhammer et al., Langmuir 10:1306-1313 (1994)). Thus, preferred A moieties include, but are not limited to, silane moieties, sulfur moieties (including alkyl sulfur moieties), and amino moieties. In a preferred embodiment, epoxide type linkages with redox polymers such as are known in the art are not used.

Although depicted herein as a single moiety, the conductive oligomer (and other spacers) may be attached to the electrode with more than one "A" moiety; the "A" moieties may be the same or different. Thus, for example, when the electrode is a gold electrode, and "A" is a sulfur atom or moiety, such as generally depicted below in Structure 13, multiple sulfur atoms may be used to attach the conductive oligomer to the electrode, such as is generally depicted below in Structures 14, 15 and 16. As will be appreciated by those in the art, other such structures can be made. In Structures 14, 15 and 16, the A moiety is just a sulfur atom, but substituted sulfur moieties may also be used.

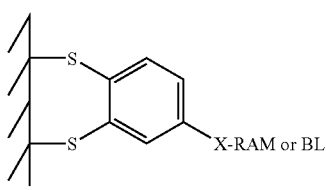

Structure 14

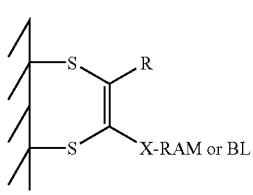

Structure 15

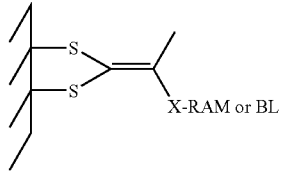

Structure 16

It should also be noted that similar to Structure 16, it may be possible to have a conductive oligomer terminating in a single carbon atom with three sulfur moieties attached to the electrode.

In a preferred embodiment, the electrode is a gold electrode, and attachment is via a sulfur linkage as is well known in the art, i.e. the A moiety is a sulfur atom or moiety. Although the exact characteristics of the gold-sulfur attachment are not known, this linkage is considered covalent for the purposes of this invention. A representative structure is depicted in Structure 17. Structure 17 depicts the "A" linker as comprising just a sulfur atom, although additional atoms may be present (i.e. linkers from the sulfur to the conductive oligomer or substitution groups).

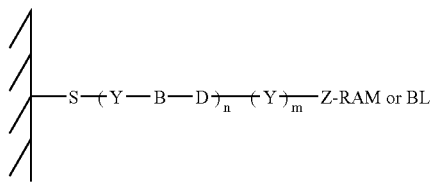

Structure 17

In a preferred embodiment, the electrode is a carbon electrode, i.e. a glassy carbon electrode, and attachment is via a nitrogen of an amine group. A representative structure is depicted in Structure 18. Again, additional atoms may be present, i.e. Z type linkers.

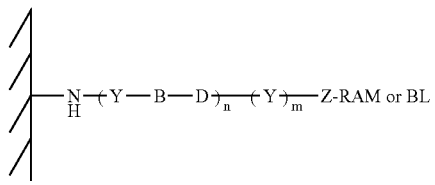

Structure 18

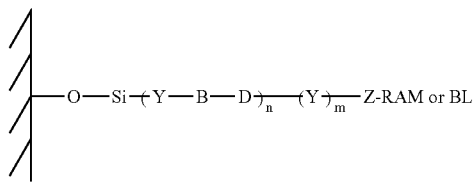

Structure 19

In Structure 19, the oxygen atom is from the oxide of the metal oxide electrode. The Si atom may also contain other atoms, i.e. be a silicon moiety containing substitution groups.

Thus, in a preferred embodiment, electrodes are made that comprise conductive oligomers attached to redox active complexes for the purposes of hybridization assays, as is more fully described herein. As will be appreciated by those in the art, electrodes can be made that have a single species of binding ligand, i.e. for the detection of a single target analyte, or multiple binding ligand species, i.e. for the detection of multiple target analytes.

In addition, as outlined herein, the use of a solid support such as an electrode enables the use of these assays in an array form. The use of arrays such as oligonucleotide arrays are well known in the art, and similar systems can be built herein. In addition, techniques are known for "addressing" locations within an electrode array and for the surface modification of electrodes. Thus, in a preferred embodiment, arrays of different binding ligands are laid down on the array of electrodes, each of which are covalently attached to the electrode via a conductive linker. In this embodiment, the number of different species of analytes may vary widely, from one to thousands, with from about 4 to about 100,000 being preferred, and from about 10 to about 10,000 being particularly preferred.

In a preferred embodiment, the electrode further comprises a passayation agent, preferably in the form of a monolayer on the electrode surface. The efficiency of binding may increase when the target analyte is at a distance from the electrode, and non-specific binding is decreased when a monolayer is used. A passayation agent layer facilitates the maintenance of the target analyte away from the electrode surface. In addition, a passayation agent serves to keep charge carriers away from the surface of the electrode. Thus, this layer helps to prevent electrical contact between the electrodes and the electron transfer moieties, or between the electrode and charged species within the solvent. Such contact can result in a direct "short circuit" or an indirect short circuit via charged species which may be present in the sample. Accordingly, the monolayer of passayation agents is preferably tightly packed in a uniform layer on the electrode surface, such that a minimum of "holes" exist. Alternatively, the passayation agent may not be in the form of a monolayer, but may be present to help the packing of the conductive oligomers or other characteristics.

The passayation agents thus serve as a physical barrier to block solvent accessibility to the electrode. As such, the passayation agents themselves may in fact be either (1) conducting or (2) nonconducting, i.e. insulating, molecules. Thus, in one embodiment, the passayation agents are conductive oligomers, as described herein, with or without a terminal group to block or decrease the transfer of charge to the electrode. Other passayation agents include oligomers of $-(CF_2)_n-$, $-(CHF)_n-$ and $-(CFR)_n-$. In a preferred embodiment, the passayation agents are insulator moieties.

An "insulator" is a substantially nonconducting oligomer, preferably linear. By "substantially nonconducting" herein is meant that the rate of electron transfer through the insulator is the rate limiting step of the transfer reaction. Stated differently, the electrical resistance of the insulator is higher than the electrical resistance of the rest of the system. The rate of electron transfer through the insulator is preferably slower than the rate through the conductive oligomers described herein. It should be noted however that even oligomers generally considered to be insulators still may transfer electrons, albeit at a slow rate.

In a preferred embodiment, the insulators have a conductivity, S, of about $10^{-7} \Omega^{-1} cm^{-1}$ or lower, with less than about $10^{-8} \Omega^{-1} cm^{-1}$ being preferred. See generally Gardner et al., supra.

Generally, insulators are alkyl or heteroalkyl oligomers or moieties with sigma bonds, although any particular insulator molecule may contain aromatic groups or one or more conjugated bonds. By "heteroalkyl" herein is meant an alkyl group that has at least one heteroatom, i.e. nitrogen, oxygen, sulfur, phosphorus, silicon or boron included in the chain. Alternatively, the insulator may be quite similar to a conductive oligomer with the addition of one or more heteroatoms or bonds that serve to inhibit or slow, preferably substantially, electron transfer.

The passayation agents, including insulators, may be substituted with R groups as defined herein to alter the packing of the moieties or conductive oligomers on an electrode, the hydrophilicity or hydrophobicity of the insulator, and the flexibility, i.e. the rotational, torsional or longitudinal flexibility of the insulator. For example, branched alkyl groups may be used. In addition, the terminus of the passayation agent, including insulators, may contain an additional group to influence the exposed surface of the monolayer. For example, there may be negatively charged groups on the terminus to form a negatively charged surface to repel negatively charged species from non-specifically binding. Similarly, for example as depicted in System 1, hydrophobic groups can be used to attract hydrophobic analytes, etc. Preferred passayation agent terminal groups include $-NH_2$, $-OH$, $-COOH$, $-CH_3$, trimethylsilyl (TMS) and (poly) ethylene glycol, with the latter being particularly preferred.

The length of the passayation agent will vary as needed. As outlined above, it appears that binding is more efficient at a distance from the surface. Thus, the length of the passayation agents is similar to the length of the conductive oligomers, as outlined above. In addition, the conductive oligomers may be basically the same length as the passayation agents or longer than them, resulting in the binding ligands being more accessible to the solvent for binding of target analytes.

The monolayer may comprise a single type of passayation agent, including insulators, or different types.

Suitable insulators are known in the art, and include, but are not limited to, $-(CH_2)_n-$, $-(CRH)_n-$, and $-(CR_2)_n-$, ethylene glycol or derivatives using other heteroatoms in place of oxygen, i.e. nitrogen or sulfur (sulfur derivatives are not preferred when the electrode is gold).

The passayation agents are generally attached to the electrode in the same manner as the conductive oligomer, and may use the same "A" linker as defined above.

The compositions of the invention are generally synthesized as outlined below, generally utilizing techniques well known in the art.

The compositions may be made in several ways. A preferred method first synthesizes a conductive oligomer attached to the binding ligand or redox active molecule, followed by attachment to the electrode. The second component of the redox active complex may be added prior to attachment to the electrode or after. Alternatively, the redox active complex may be made and then the completed conductive oligomer added, followed by attachment to the electrode. Alternatively, the conductive oligomer and monolayer (if present) are attached to the electrode first, followed by attachment of the other components.

In a preferred embodiment, conductive oligomers are covalently attached via sulfur linkages to the electrode. However, surprisingly, traditional protecting groups for use of attaching molecules to gold electrodes are generally not ideal for use in both synthesis of the compositions described herein and inclusion in biomolecule synthetic reactions. Accordingly, alternate methods for the attachment of conductive oligomers to gold electrodes, utilizing unusual protecting groups, including ethylpyridine, and trimethylsilylethyl as is described in PCT US97/20014. Briefly, in a preferred embodiment, the subunit of the conductive oligomer which contains the sulfur atom for attachment to the electrode is protected with an ethyl-pyridine or trimethylsilylethyl group. For the former, this is generally done by contacting the subunit containing the sulfur atom (preferably in the form of a sulfhydryl) with a vinyl pyridine group or vinyl trimethylsilylethyl group under conditions whereby an ethylpyridine group or trimethylsilylethyl group is added to the sulfur atom.

This subunit also generally contains a functional moiety for attachment of additional subunits, and thus additional subunits are attached to form the conductive oligomer. The conductive oligomer is then attached to a component of the redox active complex. The protecting group is then removed and the sulfur-gold covalent attachment is made. Alternatively, all or part of the conductive oligomer is made, and then either a subunit containing a protected sulfur atom is added, or a sulfur atom is added and then protected. The conductive oligomer is then attached to a component of the redox active complex. Alternatively, the conductive oligomer attached to the redox active complex component, and then either a subunit containing a protected sulfur atom is added, or a sulfur atom is added and then protected. Alternatively, the ethyl pyridine protecting group may be used as above, but removed after one or more steps and replaced with a standard protecting group like a disulfide. Thus, the ethyl pyridine or trimethylsilylethyl group may serve as the protecting group for some of the synthetic reactions, and then removed and replaced with a traditional protecting group.

By "subunit" of a conductive polymer herein is meant at least the moiety of the conductive oligomer to which the sulfur atom is attached, although additional atoms may be present, including either functional groups which allow the addition of additional components of the conductive oligomer, or additional components of the conductive oligomer. Thus, for example, when Structure 1 oligomers are used, a subunit comprises at least the first Y group.

A preferred method comprises 1) adding an ethyl pyridine or trimethylsilylethyl protecting group to a sulfur atom attached to a first subunit of a conductive oligomer, generally done by adding a vinyl pyridine or trimethylsilylethyl group to a sulfhydryl; 2) adding additional subunits to form the conductive oligomer; 3) adding at least a first component of the redox active complex to the conductive oligomer; 4) adding additional components as necessary; and 5) attaching the conductive oligomer to the gold electrode.

The above method may also be used to attach passayation molecules to a gold electrode.

In a preferred embodiment, a monolayer of passayation agents is added to the electrode. Generally, the chemistry of addition is similar to or the same as the addition of conductive oligomers to the electrode, i.e. using a sulfur atom for attachment to a gold electrode, etc. Compositions comprising monolayers in addition to the conductive oligomers covalently attached to components of the redox active complex may be made in at least one of five ways: (1) addition of the monolayer, followed by subsequent addition of the conductive oligomer-redox activecomplex; (2) addition of the conductive oligomer-redox active complex followed by addition of the monolayer; (3) simultaneous addition of the monolayer and conductive oligomer-redox active complex; (4) formation of a monolayer (using any of 1, 2 or 3) which includes conductive oligomers which terminate in a functional moiety suitable for attachment of a redox active complex; or (5) formation of a monolayer which includes conductive oligomers which terminate in a functional moiety suitable for synthesis, i.e. the redox active complex (for example, the binding ligand) is synthesized on the surface of the monolayer as is known in the art. Such suitable functional moieties include, but are not limited to, nucleosides, amino groups, carboxyl groups, protected sulfur moieties, or hydroxyl groups for phosphoramidite additions.

As will be appreciated by those in the art, electrodes may be made that have any combination of components. Thus, a variety of different conductive oligomers or passayation agents may be used on a single electrode.

Once made, the compositions find use in a number of applications, as described herein.

The compositions of the invention thus comprise assay complexes comprising a target analyte bound to a redox active complex, wherein the complex comprises a binding ligand and a redox active molecule. In a preferred embodiment, the ligand-analyte interaction is such that the environment of the redox active molecule changes sufficiently upon binding to alter a measurable redox property of the redox active molecule. For example, in antibody-antigen complexes, enzyme-substrate (or inhibitor) complexes, other protein-protein interactions, etc., the redox active molecule is generally located within or adjacent to the binding site or active site of the interaction, such that upon binding, the environment of the redox active molecule changes. This may be due to a conformational change, a "shielding" of the redox active molecule, new solvent accessibility of the redox active molecule, etc. Preferably, the redox active molecule is placed such that it does not inhibit the ligand-target binding but is affected by it. In general, the RAM is generally within less than 50 Å of the target analyte, with less than about 25 Å being preferred, and less than 6-10 Å being particularly preferred.

In general, changes in faradaic impedance are due to changes in the rate of electron transfer between the RAM, generally through the conductive oligomer, to the electrode. As predicted by semiclassical theory, changes in the rate of electron transfer can be due to changes in the intervening medium (conceptually, changes in $H_{AB}$), changes in nuclear reorganization energy, $\lambda$ (the major component of which is the solvent reorganization energy), changes in the driving force $(-)G\square$; which is generally a function of changes in the input signal, rather than changes in the system as a result of analyte binding), changes in distance, according to the following equation:

$$k_{ET} = (4B^3/\hbar^2 8k_B T)^{1/2} (H_{AB})^2 \exp[(-)G\square;+8)^2/8k_B T]$$

Thus, as generally discussed herein, changes in faradaic impedance are generally determined by evaluating the changes in the rate and/or quantity of electron transfer between the RAM and the electrode. Accordingly, changes in faradaic impedance are done by initiating electron transfer, generally both in the absence and presence of the target analyte, and evaluating the generated signal, which will be characteristic of either the absence or presence of the target analyte. In some embodiments, for example in system 8, there may be little or no electron transfer in the absence of the analyte. Other systems rely on changes in electron transfer rate or quantity on the basis of the presence or absence of the target analyte.

Electron transfer is generally initiated electronically, with the application of at least a first input signal, with voltage being preferred. A potential is applied to the assay complex. Precise control and variations in the applied potential can be via a potentiostat and either a three electrode system (one reference, one sample (or working) and one counter electrode) or a two electrode system (one sample and one counter electrode). This allows matching of applied potential to peak potential of the system which depends in part on the choice of RAMs and in part on the conductive oligomer used, the composition and integrity of the monolayer, and what type of reference electrode is used. As described herein, ferrocene is a preferred RAM.

In a preferred embodiment, a co-reductant or co-oxidant (collectively, co-redoxant) is used, as an additional electron source or sink. See generally Sato et al., Bull. Chem. Soc. Jpn 66:1032 (1993); Uosaki et al., Electrochimica Acta 36:1799 (1991); and Alleman et al., J. Phys. Chem. 100: 7050 (1996); all of which are incorporated by reference. This finds use when DC detection modes are used, or slow AC, i.e. non-diffusion limited AC.

In a preferred embodiment, an input electron source in solution is used in the initiation of electron transfer, preferably when initiation and detection are being done using DC current or at AC frequencies where diffusion is not limiting. In general, as will be appreciated by those in the art, preferred embodiments utilize monolayers that contain a minimum of "holes", such that short-circuiting of the system is avoided. This may be done in several general ways. In a preferred embodiment, an input electron source is used that has a lower or similar redox potential than the RAM of the assay complex. Thus, at voltages above the redox potential of the input electron source, both the RAM and the input electron source are oxidized and can thus donate electrons; the RAM donates an electron to the electrode and the input source donates to the RAM. For example, ferrocene, as a RAM attached to the compositions of the invention as described in the examples, has a redox potential of roughly 200 mV in aqueous solution (which can change significantly depending on what the ferrocene is bound to, the manner of the linkage and the presence of any substitution groups). Ferrocyanide, an electron source, has a redox potential of roughly 200 mV as well (in aqueous solution). Accordingly, at or above voltages of roughly 200 mV, ferrocene is converted to ferricenium, which then transfers an electron to the electrode. Now the ferricyanide can be oxidized to transfer an electron to the RAM. In this way, the electron source (or co-reductant) serves to amplify the signal generated in the system, as the electron source molecules rapidly and repeatedly donate electrons to the RAM attached to the assay complex. The rate of electron donation or acceptance will be limited by the rate of diffusion of the co-reductant, the electron transfer between the co-reductant and the RAM, which in turn is affected by the concentration and size, etc.

Alternatively, input electron sources that have lower redox potentials than the RAM are used. At voltages less than the redox potential of the RAM, but higher than the redox potential of the electron source, the input source such as ferrocyanide is unable to be oxidized and thus is unable to donate an electron to the RAM; i.e. no electron transfer occurs. Once ferrocene is oxidized, then there is a pathway for electron transfer.

In an alternate preferred embodiment, an input electron source is used that has a higher redox potential than the RAM of the label probe. For example, luminol, an electron source, has a redox potential of roughly 720 mV. At voltages higher than the redox potential of the RAM, but lower than the redox potential of the electron source, i.e. 200-720 mV, the ferrocene is oxidized, and transfers a single electron to the electrode via the conductive oligomer. However, the RAM is unable to accept any electrons from the luminol electron source, since the voltages are less than the redox potential of the luminol. However, at or above the redox potential of luminol, the luminol then transfers an electron to the RAM, allowing rapid and repeated electron transfer. In this way, the electron source (or co-reductant) serves to amplify the signal generated in the system, as the electron source molecules rapidly and repeatedly donate electrons to the RAM of the assay complex.

Luminol has the added benefit of becoming a chemiluminescent species upon oxidation (see Jirka et al., Analytica Chimica Acta 284:345 (1993)), thus allowing photo-detection of electron transfer from the RAM to the electrode. Thus, as long as the luminol is unable to contact the electrode directly, i.e. in the presence of the SAM such that there is no efficient electron transfer pathway to the electrode, luminol can only be oxidized by transferring an electron to the RAM on the assay complex. When the RAM is not present, luminol is not significantly oxidized, resulting in a low photon emission and thus a low (if any) signal from the luminol. In the presence of the target, a much larger signal is generated. Thus, the measure of luminol oxidation by photon emission is an indirect measurement of the ability of the RAM to donate electrons to the electrode. Furthermore, since photon detection is generally more sensitive than electronic detection, the sensitivity of the system may be increased. Initial results suggest that luminescence may depend on hydrogen peroxide concentration, pH, and luminol concentration, the latter of which appears to be non-linear.

Suitable electron source molecules are well known in the art, and include, but are not limited to, ferricyanide, and luminol.

Alternatively, output electron acceptors or sinks could be used, i.e. the above reactions could be run in reverse, with the RAM such as a metallocene receiving an electron from the electrode, converting it to the metallicenium, with the output electron acceptor then accepting the electron rapidly and repeatedly. In this embodiment, cobalticenium is the preferred RAM.

Changes in the faradaic impedance of the system, e.g. differences in the rate or quantity of electron transfer, can be detected in a variety of ways. A variety of detection methods may be used, including, but not limited to, optical detection (as a result of spectral changes upon changes in redox states), which includes fluorescence, phosphorescence, luminiscence, chemiluminescence, electrochemiluminescence, and refractive index; and electronic detection, including, but not limited to, amperommetry, voltammetry, capacitance and impedence. These methods include time or frequency dependent methods based on AC or DC currents, pulsed methods, lock-in techniques, filtering (high pass, low pass, band pass), and time-resolved techniques including time-resolved fluoroscence.

In one embodiment, the efficient transfer of electrons from the RAM to the electrode results in stereotyped changes in the redox state of the RAM. With many RAMs, including the complexes of ruthenium containing bipyridine, pyridine and imidazole rings, these changes in redox state are associated with changes in spectral properties. Significant differences in absorbance are observed between reduced and oxidized states for these molecules. See for example Fabbrizzi et al., Chem. Soc. Rev. 1995 pp 197-202). These differences can be monitored using a spectrophotometer or simple photomultiplier tube device.

In this embodiment, possible electron donors and acceptors include all the derivatives listed above for photoactivation or initiation. Preferred electron donors and acceptors have characteristically large spectral changes upon oxidation and reduction resulting in highly sensitive monitoring of electron transfer. Such examples include $Ru(NH_3)_4py$ and $Ru(bpy)_2im$ as preferred examples. It should be understood that only the donor or acceptor that is being monitored by absorbance need have ideal spectral characteristics.

In a preferred embodiment, the electron transfer is detected fluorometrically. Numerous transition metal complexes, including those of ruthenium, have distinct fluorescence properties. Therefore, the change in redox state of the electron donors and electron acceptors attached to the redox active complex can be monitored very sensitively using fluorescence, for example with $Ru(4,7\text{-biphenyl}_2\text{-phenanthroline})_3^{2+}$. The production of this compound can be easily measured using standard fluorescence assay techniques. For example, laser induced fluorescence can be recorded in a standard single cell fluorimeter, a flow through "on-line" fluorimeter (such as those attached to a chromatography system) or a multi-sample "plate-reader" similar to those marketed for 96-well immuno assays.

Alternatively, fluorescence can be measured using fiber optic sensors with binding ligands in solution or attached to the fiber optic. Fluorescence is monitored using a photomultiplier tube or other light detection instrument attached to the fiber optic. The advantage of this system is the extremely small volumes of sample that can be assayed.

In addition, scanning fluorescence detectors such as the FluorImager sold by Molecular Dynamics are ideally suited to monitoring the fluorescence of modified molecules arrayed on solid surfaces. The advantage of this system is the large number of electron transfer probes that can be scanned at once using chips covered with thousands of distinct binding ligands.

Many transition metal complexes display fluorescence with large Stokes shifts. Suitable examples include bis- and trisphenanthroline complexes and bis- and trisbipyridyl complexes of transition metals such as ruthenium (see Juris, A., Balzani, V., et. al. Coord. Chem. Rev., V. 84, p. 85-277, 1988). Preferred examples display efficient fluorescence (reasonably high quantum yields) as well as low reorganization energies. These include $Ru(4,7\text{-biphenyl}_2\text{-phenanthroline})_3^{2+}$, $Ru(4,4'\text{-diphenyl-2,2'-bipyridine})_3^{2+}$ and platinum complexes (see Cummings et al., J. Am. Chem. Soc. 118:1949-1960 (1996), incorporated by reference). Alternatively, a reduction in fluorescence associated with hybridization can be measured using these systems.

In a further embodiment, electrochemiluminescence is used as the basis of the electron transfer detection. With some RAMs such as $Ru^{2+}(bpy)_3$, direct luminescence accompanies excited state decay. Changes in this property are associated with ligand binding and can be monitored with a simple photomultiplier tube arrangement (see Blackburn, G. F. Clin. Chem. 37: 1534-1539 (1991); and Juris et al., supra.

In a preferred embodiment, electronic detection is used, including amperommetry, voltammetry, capacitance, and impedance. Suitable techniques include, but are not limited to, electrogravimetry; coulometry (including controlled potential coulometry and constant current coulometry); voltametry (cyclic voltametry, pulse voltametry (normal pulse voltametry, square wave voltametry, differential pulse voltametry, Osteryoung square wave voltametry, and coulostatic pulse techniques); stripping analysis (aniodic stripping analysis, cathiodic stripping analysis, square wave stripping voltammetry); conductance measurements (electrolytic conductance, direct analysis); time-dependent electrochemical analyses (chronoamperometry, chronopotentiometry, cyclic chronopotentiometry and amperometry, AC polography, chronogalvametry, and chronocoulometry); AC impedance measurement; capacitance measurement; AC voltametry; and photoelectrochemistry.

In a preferred embodiment, monitoring electron transfer is via amperometric detection. This method of detection involves applying a potential (as compared to a separate reference electrode) between the complex-conjugated electrode and a reference (counter) electrode in the sample containing target genes of interest. Electron transfer of differing efficiencies is induced in samples in the presence or absence of target analytes; that is, the presence or absence of the target analyte can result in different currents.

The device for measuring electron transfer amperometrically involves sensitive current detection and includes a means of controlling the voltage potential, usually a potentiostat. This voltage is optimized with reference to the potential of the electron donating complex on the label probe. Possible electron donating complexes include those previously mentioned with complexes of iron, osmium, platinum, cobalt, rhenium and ruthenium being preferred and complexes of iron being most preferred.

In a preferred embodiment, alternative electron detection modes are utilized. For example, potentiometric (or voltammetric) measurements involve non-faradaic (no net current flow) processes and are utilized traditionally in pH and other ion detectors. Similar sensors are used to monitor electron transfer between the RAM and the electrode. In addition, other properties of insulators (such as resistance) and of conductors (such as conductivity, impedance and capicitance) could be used to monitor electron transfer between RAM and the electrode. Finally, any system that generates a current (such as electron transfer) also generates a small magnetic field, which may be monitored in some embodiments.

It should be understood that one benefit of the fast rates of electron transfer observed in the compositions of the invention is that time resolution can greatly enhance the signal-to-noise results of monitors based on absorbance, fluorescence and electronic current. The fast rates of electron transfer of the present invention result both in high signals and stereotyped delays between electron transfer initiation and completion. By amplifying signals of particular delays, such as through the use of pulsed initiation of electron transfer and "lock-in" amplifiers of detection, and Fourier transforms.

In a preferred embodiment, electron transfer is initiated using alternating current (AC) methods. Without being bound by theory, it appears that RAMs, bound to an electrode, generally respond similarly to an AC voltage across a circuit containing resistors and capacitors. Basically, any methods which enable the determination of the nature of these complexes, which act as a resistor and capacitor, can be used as the basis of detection. Surprisingly, traditional electrochemical theory, such as exemplified in Laviron et al., J. Electroanal. Chem. 97:135 (1979) and Laviron et al., J. Electroanal. Chem. 105:35 (1979), both of which are incorporated by reference, do not accurately model the systems described herein, except for very small $E_{AC}$ (less than 10 mV) and relatively large numbers of molecules. That is, the AC current (I) is not accurately described by Laviron's equation. This may be due in part to the fact that this theory assumes an unlimited source and sink of electrons, which is not true in the present systems.

Accordingly, alternate equations were developed, using the Nernst equation and first principles to develop a model which more closely simulates the results. This was derived as follows. The Nernst equation, Equation 1 below, describes the ratio of oxidized (O) to reduced (R) molecules (number of molecules=n) at any given voltage and temperature, since not every molecule gets oxidized at the same oxidation potential.

Equation 1

$$E_{DC} = E_0 + \frac{RT}{nF} \ln \frac{[O]}{[R]} \quad (1)$$

$E_{DC}$ is the electrode potential, $E_0$ is the formal potential of the metal complex, R is the gas constant, T is the temperature in degrees Kelvin, n is the number of electrons transferred, F is faraday's constant, [O] is the concentration of oxidized molecules and [R] is the concentration of reduced molecules.

The Nernst equation can be rearranged as shown in Equations 2 and 3:

Equation 2

$$E_{DC} - E_0 + \frac{RT}{nF} \ln \frac{[O]}{[R]} \quad (2)$$

$E_{DC}$ is the DC component of the potential.

Equation 3

$$\exp^{\frac{nF}{RT}(E_{DC}-E_0)} = \frac{[O]}{[R]} \quad (3)$$

Equation 3 can be rearranged as follows, using normalization of the concentration to equal 1 for simplicity, as shown in Equations 4, 5 and 6. This requires the subsequent multiplication by the total number of molecules.

$[O]+[R]=1$      Equation 4

$[O]=1-[R]$      Equation 5

$[R]=1-[O]$      Equation 6

Plugging Equation 5 and 6 into Equation 3, and the fact that nF/RT equals 38.9 V$^{-1}$, for n=1, gives Equations 7 and 8, which define [O] and [R], respectively:

Equation 7

$$[O] = \frac{\exp^{38.9(E-E_0)}}{1 + \exp^{38.9(E-E_0)}} \quad (4)$$

Equation 8

$$[R] = \frac{1}{1 + \exp^{38.9(E-E_0)}} \quad (5)$$

Taking into consideration the generation of an AC faradaic current, the ratio of [O]/[R] at any given potential must be evaluated. At a particular $E_{DC}$ with an applied $E_{AC}$, as is generally described herein, at the apex of the $E_{AC}$ more molecules will be in the oxidized state, since the voltage on the surface is now ($E_{DC}+E_{AC}$); at the bottom, more will be reduced since the voltage is lower. Therefore, the AC current at a given $E_{DC}$ will be dictated by both the AC and DC voltages, as well as the shape of the Nernstian curve. Specifically, if the number of oxidized molecules at the bottom of the AC cycle is subtracted from the amount at the top of the AC cycle, the total change in a given AC cycle is obtained, as is generally described by Equation 9. Dividing by 2 then gives the AC amplitude.

Equation 9

$$i_{AC} = \frac{(\text{electrons at}[E_{DC} + E_{AC}]) - (\text{electrons at}[E_{DC} - E_{AC}])}{2}$$

Equation 10 thus describes the AC current which should result:

$$i_{AC} = C_0 F \omega^{1/2}([O]_{E_{DC}+E_{AC}} - [O]_{E_{DC}-E_{AC}}) \quad (6) \text{ Equation 10}$$

As depicted in Equation 11, the total AC current will be the number of redox molecules C), times faraday's constant (F), times the AC frequency ($\omega$), times 0.5 (to take into account the AC amplitude), times the ratios derived above in Equation 7. The AC voltage is approximated by the average amplitude, $E_{AC}2/\pi$.

Equation 11

$$i_{AC} = \frac{C_0 F \omega}{2} \left( \frac{\exp^{38.9\left[E_{DC}+\frac{2E_{AC}}{\pi}-E_0\right]}}{1 + \exp^{38.9\left[E+\frac{2E_{AC}}{\pi}-E_0\right]}} \right) - \frac{\exp^{38.9\left[E_{DC}-\frac{2E_{AC}}{\pi}-E_0\right]}}{1 + \exp^{38.9\left[E_{DC}-\frac{2E}{\pi}\cdot E\right]}} \quad (7)$$

However, Equation 11 does not incorporate the effect of electron transfer rate nor of instrument factors including input impedance and stray capacitance. Electron transfer rate is important when the rate is close to or lower than the applied frequency. Thus, the true $i_{AC}$ should be a function of all three, as depicted in Equation 12.

$i_{AC} = f(\text{Nernst factors}) f(k_{ET}) f(\text{instrument factors})$    Equation 12

These equations can be used to model and predict the expected AC currents in systems which use input signals comprising both AC and DC components. As outlined above, traditional theory surprisingly does not model these systems at all, except for very low voltages.

In general, non-specifically bound analytes can show differences in impedance (i.e. higher impedances) than when the analytes are specifically bound. In a preferred embodiment, the non-specifically bound material is washed away, resulting in an effective impedance of infinity. Thus, AC detection gives several advantages as is generally discussed below, including an increase in sensitivity, and the ability to "filter out" background noise. In particular, changes in impedance (including, for example, bulk impedance) as between non-specific binding of target analytes and target-specific assay complex formation may be monitored.

Accordingly, when using AC initiation and detection methods, the frequency response of the system changes as a result of the presence of the RAM. By "frequency response" herein is meant a modification of signals as a result of electron transfer between the electrode and the RAM. This modification is different depending on signal frequency. A frequency response includes AC currents at one or more frequencies, phase shifts, DC offset voltages, faradaic impedance, etc.

Once the assay complex including the target analyte is made, a first input electrical signal is then applied to the system, preferably via at least the sample electrode (containing the complexes of the invention) and the counter electrode, to initiate electron transfer between the electrode and the RAM. Three electrode systems may also be used, with the voltage applied to the reference and working electrodes. The first input signal comprises at least an AC component. The AC component may be of variable amplitude and frequency. Generally, for use in the present methods, the AC amplitude ranges from about 1 mV to about 1.1 V, with from about 10 mV to about 800 mV being preferred, and from about 10 mV to about 300 mV being especially preferred. The AC frequency ranges from about 10 Hz to about 100 KHz, with from about 10 Hz to about 10 MHz being preferred, and from about 100 Hz to about 20 MHz being especially preferred.

The use of combinations of AC and DC signals gives a variety of advantages, including surprising sensitivity and signal maximization.

In a preferred embodiment, the first input signal comprises a DC component and an AC component. That is, a DC offset voltage between the sample and counter electrodes is swept through the electrochemical potential of the RAM (for example, when ferrocene is used, the sweep is generally from 0 to 500 mV) (or alternatively, the working electrode is grounded and the reference electrode is swept from 0 to −500 mV). The sweep is used to identify the DC voltage at which the maximum response of the system is seen. This is generally at or about the electrochemical potential of the RAM. Once this voltage is determined, either a sweep or one or more uniform DC offset voltages may be used. DC offset voltages of from about −1 V to about +1.1 V are preferred, with from about −500 mV to about +800 mV being especially preferred, and from about −300 mV to about 500 mV being particularly preferred. In a preferred embodiment, the DC offset voltage is not zero. On top of the DC offset voltage, an AC signal component of variable amplitude and frequency is applied. If the RAM is present, and can respond to the AC perturbation, an AC current will be produced due to electron transfer between the electrode and the RAM.

For defined systems, it may be sufficient to apply a single input signal to differentiate between the presence and absence of the target analyte. Alternatively, a plurality of input signals are applied. As outlined herein, this may take a variety of forms, including using multiple frequencies, multiple DC offset voltages, or multiple AC amplitudes, or combinations of any or all of these.

Thus, in a preferred embodiment, multiple DC offset voltages are used, although as outlined above, DC voltage sweeps are preferred. This may be done at a single frequency, or at two or more frequencies.

In a preferred embodiment, the AC amplitude is varied. Without being bound by theory, it appears that increasing the amplitude increases the driving force. Thus, higher amplitudes, which result in higher overpotentials give faster rates of electron transfer. Thus, generally, the same system gives an improved response (i.e. higher output signals) at any single frequency through the use of higher overpotentials at that frequency. Thus, the amplitude may be increased at high frequencies to increase the rate of electron transfer through the system, resulting in greater sensitivity. In addition, this may be used, for example, to induce responses in slower systems such as those that do not possess optimal spacing configurations.

In a preferred embodiment, measurements of the system are taken at least two separate amplitudes or overpotentials, with measurements at a plurality of amplitudes being preferred. As noted above, changes in response as a result of changes in amplitude may form the basis of identification, calibration and quantification of the system. In addition, one or more AC frequencies can be used as well.

In a preferred embodiment, the AC frequency is varied. At different frequencies, different molecules respond in different ways. As will be appreciated by those in the art, increasing the frequency generally increases the output current. However, when the frequency is greater than the rate at which electrons may travel between the electrode and the RAM higher frequencies result in a loss or decrease of output signal. At some point, the frequency will be greater than the rate of electron transfer between the RAM and the electrode, and then the output signal will also drop.

In one embodiment, detection utilizes a single measurement of output signal at a single frequency. That is, the frequency response of the system in the absence of target analyte can be previously determined to be very low at a particular high frequency. Using this information, any response at a particular frequency, will show the presence of the assay complex. That is, any response at a particular frequency is characteristic of the assay complex. Thus, it may only be necessary to use a single input high frequency, and any changes in frequency response is an indication that the analyte is present, and thus that the target sequence is present.

In addition, the use of AC techniques allows the significant reduction of background signals at any single frequency due to entities other than the analytes, i.e. "locking out" or "filtering" unwanted signals. That is, the frequency response of a charge carrier or redox active molecule in solution will be limited by its diffusion coefficient and charge transfer coefficient. Accordingly, at high frequencies, a charge carrier may not diffuse rapidly enough to transfer its charge to the electrode, and/or the charge transfer kinetics may not be fast enough. This is particularly significant in embodiments that do not have good monolayers, i.e. have partial or insufficient monolayers, i.e. where the solvent is accessible to the electrode. As outlined above, in DC techniques, the presence of "holes" where the electrode is accessible to the solvent can result in solvent charge carriers "short circuiting" the system, i.e. the reach the electrode and generate background signal. However, using the present AC techniques, one or more frequencies can be chosen that prevent a frequency response of one or more charge carriers in solution, whether or not a monolayer is present. This is particularly significant since many biological fluids such as blood contain significant amounts of redox active molecules which can interfere with amperometric detection methods.

In a preferred embodiment, measurements of the system are taken at least two separate frequencies, with measurements at a plurality of frequencies being preferred. A plurality of frequencies includes a scan. For example, measuring the output signal, e.g., the AC current, at a low input frequency such as 1-20 Hz, and comparing the response to the output signal at high frequency such as 10-100 kHz will show a frequency response difference between the presence and absence of the RAM. In a preferred embodiment, the frequency response is determined at least two, preferably at least about five, and more preferably at least about ten frequencies.

After transmitting the input signal to initiate electron transfer, an output signal is received or detected. The presence and magnitude of the output signal will depend on a number of factors, including the overpotential/amplitude of the input signal; the frequency of the input AC signal; the composition of the intervening medium; the DC offset; the environment of the system; the nature of the RAM; the solvent; and the type and concentration of salt. At a given input signal, the presence and magnitude of the output signal will depend in general on the presence or absence of the target analyte, the placement and distance of the RAM from the surface of the monolayer and the character of the input signal. In some embodiments, it may be possible to distinguish between non-specific binding of materials and the formation of target specific assay complexes, on the basis of impedance.

In a preferred embodiment, the output signal comprises an AC current. As outlined above, the magnitude of the output current will depend on a number of parameters. By varying these parameters, the system may be optimized in a number of ways.

In general, AC currents generated in the present invention range from about 1 femtoamp to about 1 milliamp, with currents from about 50 femtoamps to about 100 microamps being preferred, and from about 1 picoamp to about 1 microamp being especially preferred.

In a preferred embodiment, the output signal is phase shifted in the AC component relative to the input signal. Without being bound by theory, it appears that the systems of the present invention may be sufficiently uniform to allow phase-shifting based detection. That is, the complex biomolecules of the invention through which electron transfer occurs react to the AC input in a homogeneous manner, similar to standard electronic components, such that a phase shift can be determined. This may serve as the basis of detection between the presence and absence of the analyte and/or differences between the presence of target-specific assay complexes and non-specific binding of materials to the system components.

The output signal is characteristic of the presence of the analyte; that is, the output signal is characteristic of the presence of the target-specific assay complex. In a preferred embodiment, the basis of the detection is a difference in the faradaic impedance of the system as a result of the formation of the assay complex. Of importance in the methods of the invention is that the faradaic impedance between the RAM and the electrode may be significantly different depending on whether the targets are specifically or non-specifically bound to the electrode.

Accordingly, the present invention further provides electronic devices or apparatus for the detection of analytes using the compositions of the invention. The apparatus includes a test chamber for receiving a sample solution which has at least a first measuring or sample electrode, and a second measuring or counter electrode. Three electrode systems are also useful. The first and second measuring electrodes are in contact with a test sample receiving region, such that in the presence of a liquid test sample, the two electrodes may be in electrical contact.

In a preferred embodiment, the apparatus also includes detection electrodes comprising the compositions of the invention, including redox active complexes including binding ligands and redox active molecules, and a monolayer comprising conductive oligomers, such as are described herein.

The apparatus further comprises an AC voltage source electrically connected to the test chamber; that is, to the measuring electrodes. Preferably, the AC voltage source is capable of delivering DC offset voltage as well.

In a preferred embodiment, the apparatus further comprises a processor capable of comparing the input signal and the output signal. The processor is coupled to the electrodes and configured to receive an output signal, and thus detect the presence of the target.

Thus, the compositions of the present invention may be used in a variety of research, clinical, quality control, or field testing settings.

In a preferred embodiment, viral and bacterial detection is done using the complexes of the invention. In this embodiment, binding ligands (for example antibodies or fragments thereof) are designed to detect targets (for example surface proteins) from a variety of bacteria and viruses. For example, current blood-screening techniques rely on the detection of anti-HIV antibodies. The methods disclosed herein allow for direct monitoring of circulating virus within a patient as an improved method of assessing the efficacy of anti-viral therapies. Similarly, viruses associated with leukemia, HTLV-I and HTLV-II, may be detected in this way. Bacterial infections such as tuberculosis, clymidia and other sexually transmitted diseases, may also be detected. Similarly, the compositions of the invention find use as probes for toxic bacteria in the screening of water and food samples. Similarly, bioremediation strategies may be evaluated using the compositions of the invention.

The present invention provides methods which can result in sensitive detection of target analytes. In a preferred embodiment, less than about $10^{12}$ molecules are detected, with less than about $10^{10}$ being preferred, less than $10^8$ being particularly preferred, less than about $10^5$ being especially preferred, and less than about $10^4$ being most preferred.

All references cited herein are incorporated by reference in their entirety.

We claim:

1. An apparatus for the detection of a non-nucleic acid target analyte in a test sample, comprising:
    a) a test chamber comprising gold electrodes, each electrode comprises:
        a covalently attached passivation species comprising a protein binding ligand;
            wherein said protein binding ligand is covalently attached to said electrode via a spacer,
            wherein said spacer is attached to said electrode with more than one sulfur moiety, and
        wherein said test chamber further comprises at least one second measuring electrode,
    b) a voltage source electrically connected to said test chamber; and
    c) an electronic detector.

2. The apparatus according to claim 1, further comprising a processor coupled to said electrodes and configured to receive an output signal.

3. The apparatus according to claim 1, wherein said spacer is attached to said electrode using two sulfur moieties.

4. The apparatus according to claim 1, wherein said protein binding ligand comprises a protein.

5. The apparatus according to claim 4, wherein said protein is a peptide.

6. The apparatus according to claim 1, wherein said protein binding ligand comprises a substrate of an enzyme.

7. The apparatus according to claim 1, wherein said passivation species comprises an insulator.

8. The apparatus according to claim 7, wherein said insulator comprises a C1 to C12 alkyl group.

9. The apparatus according to claim 1, wherein said passivation species comprises a conductive oligomer.

* * * * *